United States Patent
Lowdell

(10) Patent No.: US 8,257,970 B2
(45) Date of Patent: Sep. 4, 2012

(54) METHOD FOR ACTIVATING NATURAL KILLER CELLS BY TUMOR CELL PREPARATION IN VITRO

(75) Inventor: Mark Lowdell, Beaumont-cum-Moze (GB)

(73) Assignee: UCL Biomodica PLC, London (GB)

( * ) Notice: Subject to any disclaimer, the term of this patent is extended or adjusted under 35 U.S.C. 154(b) by 1040 days.

(21) Appl. No.: 11/856,466

(22) Filed: Sep. 17, 2007

(65) Prior Publication Data

US 2008/0166326 A1    Jul. 10, 2008

Related U.S. Application Data

(63) Continuation-in-part of application No. PCT/GB2006/000960, filed on Mar. 16, 2006.

(30) Foreign Application Priority Data

Mar. 17, 2005 (GB) .................................. 0505508.2
Jul. 12, 2005 (GB) .................................. 0514288.0

(51) Int. Cl.
  C12N 5/00  (2006.01)
  C12N 5/07  (2010.01)

(52) U.S. Cl. ........ 435/325; 435/347; 435/372; 435/373; 435/377; 424/93.1; 424/93.3; 424/93.7

(58) Field of Classification Search .................. 435/325, 435/347, 372, 373, 377; 424/93.1, 93.3, 424/93.7
See application file for complete search history.

(56) References Cited

U.S. PATENT DOCUMENTS 6,849,452 B1 * 2/2005 Zitvogel et al. ............... 435/347
7,435,596 B2 * 10/2008 Campana et al. ............. 435/455

OTHER PUBLICATIONS

Stefan W. Krause, et al., Treatment of Colon and Lung Cancer Patients with ex Vivo Heat Shock Protein 70-Peptide-Activated, Autologous Natural Killer Cells: A Clinical Phase I Trial, Clinical Cancer Research (2004) vol. 10, p. 3699-3707.
Kazuyoshi Takeda, et al., CD27-Mediated Activation of Murine NK Cells[1], The Journal of Immunology (2000) vol. 164, p. 1741-1745.
Brown, M. H., et al., "2B4, the Natural Killer and T Cell Immunoglobulin Superfamily Surface Protein, is a Ligand for CD48," J. Exp. Med., 188:2083-2090 (1998).
Demanet, et al., "Down-regulation of HLA-A and HLA-Bw6, but not HLA-Bw4, allospecificities in leukemic cells: an escape mechanism from CLT and NK attack?" Blood, 103:3122-3130 (2004).
Drexler, HG, et al., "Malignant hematopoietic cell lines: in vitro models for the study of MLL gene alterations," Leukemia, 18:227-232 (2004).
Esplugues, et al., "Enhanced Antitumour Immunity in Mice Deficient in CD69," J. Exp. Med., 197:1093-1106 (2003).
Esplugues, et al., "Induction of tumor NK-cell immunity by anti-CD69 antibody therapy," Blood, 105(11):4399-4406 (2005).
Greil, J., et al., "The acute lymphoblastic leukaemia cell line SEM with t(4;11) chromosomal rearrangement is biphenotypic and responsive to interleukin-7," Br. J. Haematol., 86(2):275-83 (1994).
Lange, et al., "Growth factor requirements of childhood acute leukemia: establishement of GM-CSF-dependent cell lines," Blood, 70:192-99 (1987).
Leppa, S., et al., "Differential Induction of Hsp70-encoding genes in human haematopoietic cells," J. Biological Chemistry, 276(34):31713-31719 (2001).
Lowdell, et al., "Evidence that continued remission in patients treated for acute leukaemia is dependent on autologous natural kill cells," British Journal of Haematology, 117:821-7 (2002).
Lowdell, et al., "The effect of T cell depletion with Campath-1M on immune reconstitution after chemotherapy and allogeneic bone marrow transplant as treatment for leukaemia," Bone Marrow Transplant, 21:679-686 (1998).
Lowdell, M.W., "Natural killer cells in haematopoietic stem cell transplantation," Transfusion Medicine, 13:399-404 (2003).
Miller, et al., "Low dose subcutaneous interleukin-2 after autologous transplantation generates sustained in vivo natural killer cell activity," Biol. Blood Marrow Transplant., 3:34-44 (1997).
Miller, J.S., et al., "Successful adoptive transfer and in vivo expansion of human haploidentical NK cells in cancer patients," Blood, republished online Jan. 4, 2005, DOI 10. 1182/blood-2004-07-2974.
North, J., et al., "Tumor-primed human natural killer cells lyse NK-resistant tumor targets: evidence of a two-stage process in resting NK cell activation," J. Immunol., 178(1):85-94 (2007).
Orleans-Lindsay, J. K., et al., "Acute myeloid leukaemia cells secrete a soluble factor that inhibits T and NK cell proliferation but not cytolytic function—implications for the adoptive immunotherapy of leukaemia," Clin. Exp. Immunol., 126:403-411 (2001).
Penack, O., et al., "CD56dimCDneg cells are responsible for natural cytotoxicity against tumor targets," Leukemia, 19(5):835-840 (2005).
Pisegna, et al., "Src-Dependent Syk Activation Controls CD69-Mediated Signaling and Function on Human NK Cells," J. Immunology, 169:68-74 (2002).
Porgador, A., et al., "Bone marrow-generated dendritic cells pulsed with a class I-restricted peptide are potent inducers of cytotoxic T lymphocytes," J. Exp. Med. 182:255-260 (1995).
Reichel, et al., "Fine structure of translocation breakpoints in leukemic blasts with chromosomal translocation t(441): the DNA damage-repair model of translocation," Oncogene, 17:3035-44 (1998).
Reittie, et al., "Endogenously generated activated killer cells circulate after autologous and allogeneic marrow transplantation but not after chemotherapy," Blood, 73:1351-1358 (1989).
Rosenberg, et al., "A progress report on the treatment of 157 patients with advanced cancer using lymphokine-activated killer cells and interleukin-2 or high-dose interleukin-2 alone," N. Engl. J. Med., 316:889-897 (1987).
Ruggeri, et al., "Effectiveness of Donor Nature Killer Cell Alloreactivity in Mismatched Hematopoietic Transplants," Science, 295:2097-2100 (2002).

(Continued)

*Primary Examiner* — Ruth Davis
(74) *Attorney, Agent, or Firm* — Todd Lorenz; Arnold & Porter LLP

(57) ABSTRACT

The present invention provides a method for activating a Natural Killer (NK) cell by contacting the NK cell in vitro with an activating tumor cell preparation (ATCP). The invention also provides an activated NK cell produced by such a method and its use in the treatment of cancer.

5 Claims, 19 Drawing Sheets

OTHER PUBLICATIONS

Santoli, et al., "Synergistic and antagonistic effects of recombinant human interleukin (IL) 3, IL-1 alpha, granulocyte and macrophage colony-stimulating factors (G-CSF and M-CSSF) on the growth of GM-CSF-dependent leukemic cell lines," J. Immunol., 139:3348-54 (1987).

Yu, et al., "The role of Ly49A and 5E6(Ly49C) molecules in hybrid resistance mediated by murine natural killer cells against normal T cell blasts," Immunity, 4:67-76 (1996).

Zou J.-P., "Tumor-immunotherapy with the use of tumor-antigen-pulsed antigen-presenting cells," Cancer Immunol. Imnnunother., 35:1-6 (1992).

Extended European Search Report, European Patent Office, regarding corresponding divisional European Application No. 11002652, held in the name of UCL Business PLC, mailed on Nov. 29, 2011.

Examination Report, European Patent Office, regarding corresponding European Application No. 06726410, held in the name of UCL Business PLC, mailed Nov. 15, 2011.

Carson, W., et al., "Interleukin-2 enhances the natural killer cell response to Herceptin-coated Her2/neu-positive breast cancer cells," European J. of Immunol., 31(10):3016-25 (2001).

Craston, R., et al., "Temporal dynamics of CD69 expression on lymphoid cells," J. Immunol. Methods, 209(1):37-45 (1997).

Das A., et al., "Modulation of NK cell activation and interaction with target cells," PINSA-B, 68(1):47-60 (2002).

Hallet, W. HD., "Natural killer cells: biology and clinical use in cancer therapy," Cellular and Molecular Immunol., 1:12-21 (2004).

Saudemont, A., et al., "NK cells that are activated by CXCL10 can kill dormant tumor cells that resist CTL-mediated lysis and can express B7-H1 that stimulates T cells," Blood, 105(6):2428-35 (2005).

Takeda, et al., "CD27-mediated activation of murine NK cells," J. Immunol., 164(4):1741-45 (2000).

* cited by examiner

A

B

A

B

A

B

A

B

C

D

E

Whole CTV-1
JN 328208.001

Post freeze/thaw
JN 328208.005

Post sonication
JN 328208.014

SEQUENCE LISTING

```
<160> NUMBER OF SEQ ID NOS: 4

<210> SEQ ID NO 1
<211> LENGTH: 32
<212> TYPE: DNA
<213> ORGANISM: Artificial Sequence
<220> FEATURE:
<223> OTHER INFORMATION: Oligonucleotide primer

<400> SEQUENCE: 1
gcgcctcgag caatacaatt gtccaggcca at                                    32

<210> SEQ ID NO 2
<211> LENGTH: 32
<212> TYPE: DNA
<213> ORGANISM: Artificial Sequence
<220> FEATURE:
<223> OTHER INFORMATION: Oligonucleotide primer

<400> SEQUENCE: 2
cgcgaagctt attatttgta aggtttgtta ca                                    32

<210> SEQ ID NO 3
<211> LENGTH: 66
<212> TYPE: DNA
<213> ORGANISM: Artificial Sequence
<220> FEATURE:
<223> OTHER INFORMATION: Oligonucleotide primer

<400> SEQUENCE: 3
catatgcatg cgggcggcct gaatgaaatt ctggatggca tgaaaatgct gtatcatgaa      60
ctcgag                                                                 66

<210> SEQ ID NO 4
<211> LENGTH: 66
<212> TYPE: DNA
<213> ORGANISM: Artificial Sequence
<220> FEATURE:
<223> OTHER INFORMATION: Oligonucleotide primer

<400> SEQUENCE: 4
ctcgagttca tgatacagca ttttcatgcc atccagaatt tcattcaggc cgcccgcatg      60
catatg                                                                 66
```

METHOD FOR ACTIVATING NATURAL KILLER CELLS BY TUMOR CELL PREPARATION IN VITRO

CROSS REFERENCE TO RELATED APPLICATIONS

This application is a continuation-in-part of International Application No. PCT/GB2006/000960, filed on Mar. 16, 2006, published as WO 2006/097743 on Sep. 21, 2006, and claiming priority to GB application Serial No. 0505508.2, filed on Mar. 17, 2005, and to GB application Serial No. 0514288.0, filed on Jul. 12, 2005.

All of the foregoing applications, as well as all documents cited in the foregoing applications ("application documents") and all documents cited or referenced in the application documents are incorporated herein by reference. Also, all documents cited in this application ("herein-cited documents") and all documents cited or referenced in herein-cited documents are incorporated herein by reference. In addition, any manufacturer's instructions or catalogues for any products cited or mentioned in each of the application documents or herein-cited documents are incorporated by reference. Documents incorporated by reference into this text or any teachings therein can be used in the practice of this invention. Documents incorporated by reference into this text are not admitted to be prior art.

FIELD OF THE INVENTION

The present invention relates to a method for activating a Natural Killer (NK) cell. In particular, it relates to a method for activating an NK cell such that it has the capacity to lyse an NK-resistant cancer cell.

BACKGROUND TO THE INVENTION

A number of cancers are, at present, incurable. For others, chemotherapy is only partially effective and a significant proportion of patients relapse following treatment. Some haematological malignancies are treatable by hematopoietic stem cell transplantation (HSCT), but fewer than 30% of patients requiring HSCT have a suitable donor and are the requisite age.

Natural Killer (NK) cells are a subset of peripheral blood lymphocytes which can spontaneously lyse certain tumour cells. The use of NK cells in adoptive tumour immunotherapy has been proposed, and there has been interest in the in vitro or ex vivo stimulation of NK cells to increase their capacity to lyse tumour cells.

The discovery of interleukin-2 (IL-2) and its role in NK-cell activation in the 1980's led to considerable interest in the use of lymphokine-activated killer (LAK) cells in tumour immunotherapy. The results of these trials were, however, largely disappointing. In a study investigating the effect of administering autologous LAK cells to patients along with IL-2, less than 20% of patients responded (Rosenburg et al (1987) N. Engl. J. Med. 316: 889-897). In studies using daily IL-2 administrations to cancer patients along with chemotherapy and autologous HCT, it was shown that, although IL-2 significantly expanded the number of circulating MK cells in vivo, the cells are not maximally cytotoxic according to an in vitro assay (Miller et al (1997) Biol. Blood Marrow Transplant. 3: 34-44).

NK cells are now known to be controlled by both positive and negative cytolytic signals. A number of molecules which mediate NK cell inhibition have been cloned over the past ten years and their ligands are almost exclusively Class I MHC molecules. Some of these receptors ("KIRs") are specific for determinants shared by certain class I alleles, and each KIR is expressed by a subset of NK cells. Therefore, in the NK repertoire, some NK cells recognise, and are blocked by, specific class I alleles. NK cells have a limited view of class I polymorphism but cells can be responsible for alloreactions when the mismatched target cells do not express the class I alleles which block every NK cell in the repertoire (the "missing-self" hypothesis). Thus allogeneic target cells which lack at least one of the class I allele groups expressed by the donor cells will not find the inhibitory class I ligand on a subset of donor NK cells and their lytic pathway will be activated.

It has thus been suggested that autologous NK cells may be suppressed by the physiologic response resulting from NK cell recognition of "self" MHC molecules.

It has also been suggested that the greater the degree of KIR mismatch with tumour MHC (i.e. KIR ligand) the greater tumour kill (Ruggeri et al (2002) Science 295:2097-2100). In view of the shortcomings of autologous NK cell therapy (thought to be due to a lack of NK cell inhibitory receptor mismatching with autologous tumour cells) the use of allogeneic NK cell infusions has been suggested as an alternative (Miller et al (2005) Blood in press, but pre-published on-line on Jan. 4, 2005).

Miller et al (2005, as above) administered IL-2 activated allogeneic haploidentical NK cells to patients with metastatic melanoma, metastatic renal cell carcinoma, refractory Hodgkin's disease or poor prognosis AML. Importantly, their results demonstrate that the NK cells can persist and expand in vivo. The cells induced complete hematologic remission in five of the 19 poor prognosis AML patients, but no activity against the other tumours. In the group which achieved remission, patients are stratified into those with predicted graft versus host alloreactivity using the KIR ligand mismatch strategy. The results showed remission was much more likely in those patients which are KIR ligand mismatched.

Non-specifically activated NK cells may therefore have an application against a subset of tumours, but the donor cells must be allogeneic and much more likely to be effective if they are HLA mismatched. A disadvantage associated with using mismatched NK cells is that they may target and reject normal (e.g. host) hematopoeitic cells (Yu et al (1996) Immunity 4:67-76).

There is thus a need for alternative immunotherapy for cancer which is effective against "NK resistant" tumours but which spares normal hematopoietic cells.

SUMMARY OF THE INVENTION

The current dogma is that NK cells are stimulated by the target cell which they ultimately lyse and that "NK-resistant" tumours are not lysed because they fail to provide this stimulus.

Contrary to current thinking, the present inventors have shown that the "stimulation event" can be temporally separated from the "lytic event". They have also shown that some tumour cells, or membrane preparations thereof, are capable of stimulating NK cells such that they can then go on to lyse a target cell which is resistant to lysis by an equivalent unstimulated NK cell.

In a first aspect, the present invention provides a method for activating an NK cell, which may comprise the step of contacting the NK cell in vitro with an activating tumour cell preparation (ATCP).

The NK cell may be activated to lyse a target cell. For example, the NK cell may be activated such that it is capable of lysing a cell previously resistant to NK-cell lysis. The present invention therefore may provide NK cells useful in the treatment of a number of "NK-resistant" malignancies, many of which are incurable at present (such as myeloma and Chronic lymphocytic leukemia (CLL)).

The fact that the "stimulation event" can be separated from the "lytic event" has the advantage that the NK cell can be stimulated in vitro, but once stimulated retains the capacity to lyse a target cell until it encounters the target cell when introduced or returned to the subject.

This form of activation may render the NK cell capable of lysing multiple tumour types which are regarded as resistant to NK cell killing. Moreover the activated NK cells may be effective irrespective of the degree of HLA matching between the NK and tumour cells. This opens up the possibility of using autologous or HLA-matched allogeneic donor NK cells. The use of autologous or HLA-matched cells may have the advantage that it is less likely to result in rejection of donor or host (e.g. host normal haematopoietic) cells.

Moreover, since the method of the invention may not rely on IL-2 mediated activation, it can avoid the adverse effects in vivo associated with the IL-2 response (Miller et al (2005) as above).

In the first aspect of the invention, the ATCP may be a preparation of, or comprise intact tumour cells. The cells may be irradiated or fixed.

Alternatively the ATCP may be or comprise a cell membrane preparation. Use of cell membranes is advantageous as it bypasses many safety concerns associated with the use of tumour cells.

The ATCP may comprise tumour cells or preparations thereof with NK activating ability, such as CTV-1 myeloid leukemia cells and/or a membrane preparation thereof.

In a second aspect, the present invention may provide an activated NK cell produced by the method of the first aspect of the invention.

Donor NK cells may be haploidentical. Donor NK cells may be HLA matched or mismatched.

Activated NK cells of the second aspect of the invention may be used to treat cancer.

In a third aspect, therefore, the present invention may provide the use of a composition comprising an activated NK cell of the second aspect of the invention in the manufacture of a medicament for the treatment of cancer. Alternatively, the third aspect may provide a method of manufacturing a medicament for the treatment of cancer involving the composition comprising an activated NK cell of the second aspect of the invention.

The approach is particularly suitable in cases where the subject is unsuited to intensive cancer treatment.

The cancer may, for example be: Acute myeloid leukaemia (AML); Chronic lymphocytic leukemia (CLL); Lymphoma; or Breast cancer.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following Detailed Description, given by way of example, but not intended to limit the invention to specific embodiments described, may be understood in conjunction with the accompanying drawings, incorporated herein by reference. Various preferred features and embodiments of the present invention will now be described by way of non-limiting example and with reference to the accompanying drawings in which.

DETAILED DESCRIPTION

Natural Killer (NK) Cell

Figure 1:
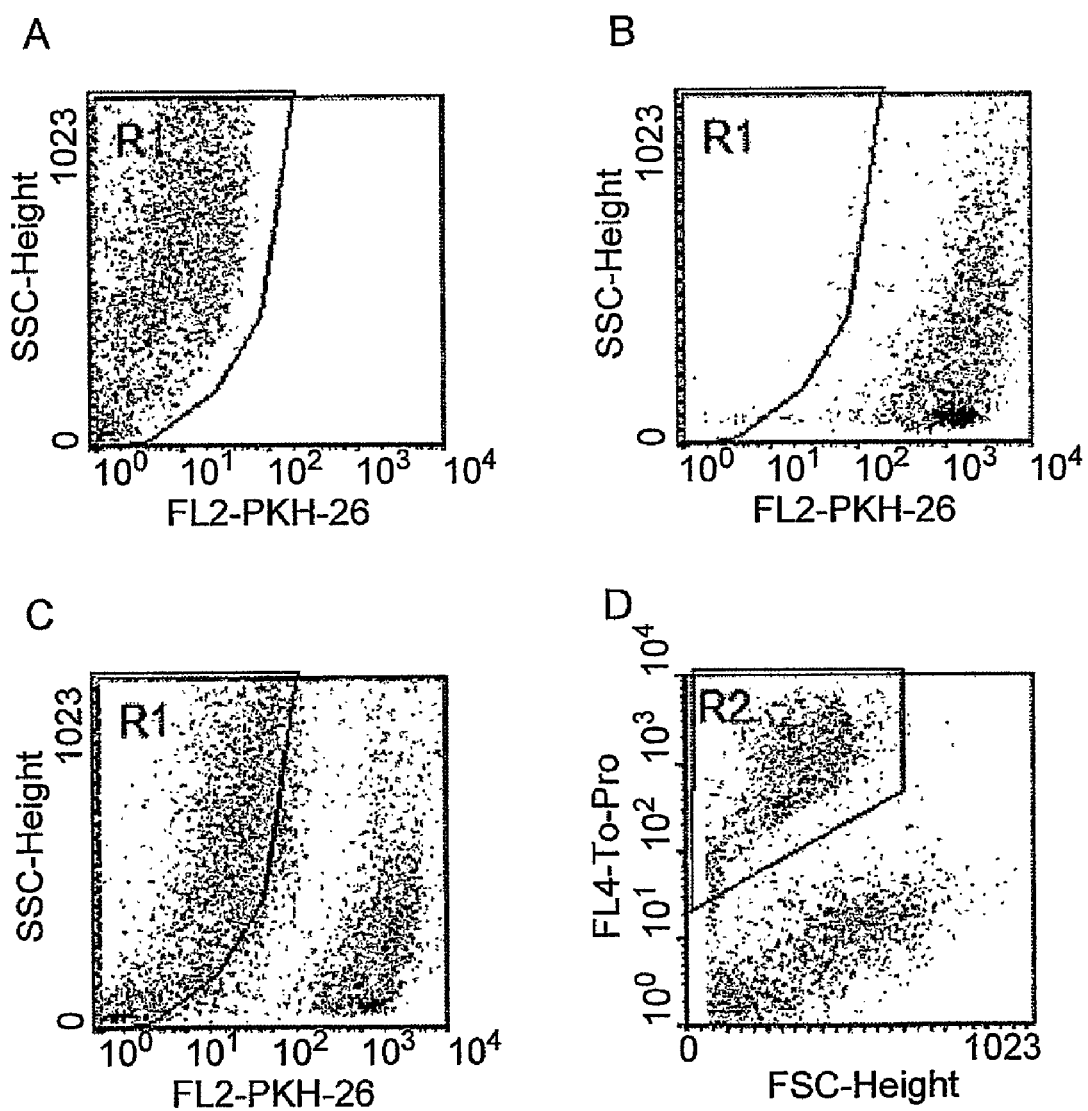
FIG. 1 is a flow cytometric dot-plot showing the analysis strategy for measurement of target cell lysis. Analysis Region 1 (R1) is established to include target cells (PKH-26-ve) (A—target cells alone) which excludes effector NK cells and stimulator AML cells pre-labeled with PKH-26 (B—effector+stimulator cells alone). This gating strategy effectively discriminates the target and effector cell populations in the admixture (C). Gating on the target cells within the admixture (R1) allows enumeration of the $FSC^{low}$/To-Pro+ "dead" targets (R2) from the To-Pro-ve live target cells (D).

The present invention relates to a method for activating a NK cell and an NK cell activated by such a method.

NK cells are a subset of peripheral blood lymphocytes defined by the expression of CD56 or CD16 and the absence of the T cell receptor (CD3). They recognise and kill transformed cell lines without priming in an MHC-unrestricted fashion.

NK cells represent the predominant lymphoid cell in the peripheral blood for many months after allogeneic or autologous stem cell transplant and they have a primary role in immunity to pathogens during this period (Reittie et al (1989) Blood 73: 1351-1358; Lowdell et al (1998) Bone Marrow Transplant 21: 679-686). The role of NK cells in engraftment, graft-versus-host disease, anti-leukemia activity and post-transplant infection is reviewed in Lowdell (2003) Transfusion Medicine 13:399-404.

Human NK cells mediate the lysis of tumour cells and virus-infected cells via natural cytotoxicity and antibody-dependent cellular cytotoxicity (ADCC).

Human NK are controlled by positive and negative cytolytic signals. Negative (inhibitory) signals are transduced by C-lectin domain containing receptors CD94/NKG2A and by some Killer Immunoglobulin-like Receptors (KIRs). The regulation of NK lysis by inhibitory signals is known as the "missing self" hypothesis in which specific HLA-class I alleles expressed on the target cell surface ligate inhibitory receptors on NK cells. The down-regulation of HLA molecules on tumor cells and some virally infected cells (e.g. CMV) lowers this inhibition below a target threshold and the target cells becomes susceptible to NK cell-mediated lysis.

Inhibitory receptors fall into two groups, those of the Ig-superfamily called Killer Immunoglobulin-like Receptors (KIRs) and those of the lectin family, the NKG2, which form dimers with CD94 at the cell surface. KIRs have a 2- or 3-domain extracellular structure and bind to HLA-A, -B or -C. The NKG2/CD94 complexes ligate HLA-E.

Inhibitory KIRs have up to 4 intracellular domains which contain ITIMs and the best characterized are KIR2DL1, KIR2DL2 and KIR2DL3 which are known to bind HLA-C molecules. KIR2DL2 and KIR2DL3 bind the group 1 HLA-C alleles whilst KIR2DL1 binds to group 2 alleles. Certain leukemia/lymphoma cells express both group 1 and 2 HLA-C alleles and are known to be resistant to NK-mediated cell lysis As regards to positive activating signals, ADCC is thought to be mediated via CD16, and a number of triggering receptors responsible for natural cytotoxicity have been identified, including CD2, CD38, CD69, NKRP-1, CD40, B7-2, NK-TR, NKp46, NKp30 and NKp44. In addition, several KIR molecules with short intracytoplasmic tails are also stimulatory. These KIRs (KIR2DS1, KIR2DS2 and KIR2DS4) are known to bind to HLA-C; their extracellular domains being identical to their related inhibitory KIRs. The activatory KIRs lack the ITIMs and instead associate with DAP12 leading to NK cell activation. The mechanism of control of expression of inhibitory versus activatory KIRs remains unknown.

The NK cells of the present invention may be autologous or allogeneic NK cell.

"Autologous" NK cells are cells derived from the patient. "Allogeneic" NK cells are derived from another individual, having non-identical gene at one or more loci. If the NK cells are derived from an identical twin, they may be termed "syngeneic".

Donor NK cells may be HLA-KIR matched or mismatched. The present inventors have shown that the degree of matching between the NK cells and target tumour cells is of no significance.

Activating Tumour Cell Preparation (ATCP)

The term "activating" is used synonymously with the term "stimulating" in this section, and throughout the document.

The present inventors have found that certain tumour cells have the capacity to stimulate NK cells to increase their capacity to lyse tumour cells. Stimulated NK cells have been shown to be capable of lysing "NK-resistant" tumour cell (i.e. tumour cells resistant to lysis with unstimulated NK cells.

Tumour cells capable of activating NK cells in this manner include CTV-1 cells. This cell line is commercially available, for example from the American Typed Cell Collection (ATCC).

It is expected that other tumour cells will also have the capacity to activate NK cells. The present invention also provides a method for determining whether a tumour cell preparation is an activating tumour cell preparation, the method having the following steps:
 (i) contacting the tumour cell preparation with a NK cell;
 (ii) contacting the NK cell from step (i) with a target cell resistant to lysis by non-activated NK cells;
 (iii) determining whether the target cell is lysed by the NK cell from step (i).

It is thus possible for a skilled person to establish whether a given tumour cell has the capacity to act as an activating tumour cell preparation and to screen known tumour cells for this activity.

The present inventors have shown that pre-incubation of NK cells with an ATCP (such as CTV-1 AML blasts) causes rapid upregulation of CD69 on the NK cells. They have also shown (using labelled CD69) that tumour cells which are lysable by activated NK cells express CD69 ligand (CD69L), but this expression is absent from cells which are not lysed (such as B cells). The presence of recombinant CD69 inhibits the capacity of activated NK cells to lyse tumour cells, presumably because it blocks interaction with CD69L on the tumour cells.

Without wishing to be bound by theory, the present inventors believe that CD69 on stimulated NK cells is the predominant trigger molecule for their cytotoxic activity.

In a preferred embodiment the ATCP used in the method of the present invention causes upregulation of expression of CD69 on the NK cell.

Although the nature of CD69 ligand(s) is, at present, unknown, it is possible to determine its expression on a candidate tumour target cells by standard techniques. For example, using CD69 labelled with a fluorochrome, it is possible to determine expression of CD69L by techniques such as flow cytometry or confocal microscopy.

The present invention thus provides a method for determining whether a tumour cell preparation is an activating tumour cell preparation, the method having the following steps:
 (i) contacting the tumour cell preparation with a NK cell;
 (ii) determining whether the TCP causes upregulation of CD69 on the NK cell.

The present invention also provides a method for determining whether a tumour cell preparation is an activating tumour cell preparation, which comprises the step of determining whether the TCP comprises or expresses CD69L.

The ATCP may consist of or comprise a population of intact tumour cells. For example, the activating tumour cell preparation may be a tumour cell line.

The ATCP may consist of or comprise a cell membrane preparation. For example, a cell membrane preparation may be made by standard fixation techniques (such as using paraformaldehyde). Fixation has the advantage that the preparation is stabilised, has a much longer "shelf-life" and is easier to store. A suitable cell membrane preparation may also be made by repeated cycles of freeze-thawing, in combination with DNAse treatment. Such a preparation may be considered to have increased safety as it reduces the likelihood of contamination associated with prions etc.

The stimulator cells may be irradiated prior to use, by standard techniques.

Membrane preparations have the advantage over preparations comprising intact tumour cells as they avoid the risk of transferring potentially malignant tumour cells to the patient.

The ATCP may be or comprise an entity (such as a protein) derivable from a tumour cell. The ATCP may, for example, comprise a recombinant protein. The protein may be derivable from CTV-1 cells.

The ATCP and the NK cell preparation may be brought together by, for example, co-culturing (where intact tumour cells are used). The "activation time" will depend on the nature of the cell preparations and the contact conditions, but may commonly be 12-24 hours, perhaps 20 hours.

Composition

The present invention also provides a composition comprising a plurality of such activated NK cells.

The composition may comprise or consist essentially of autologous and/or allogeneic NK cells.

Allogeneic NK cells may be HLA mismatched.

Allogenic NK may be obtained from peripheral blood from a donor individual. Allogeneic peripheral blood mononuclear cells may be collected by standard techniques (e.g. conventional apheresis). To minimize the possibility of graft versus host disease and immune mediated aplasia, allogeneic cells may be depleted of T cells. For example, the cell preparation may be depleted of CD3+ T-cells using microbeads conjugated with monoclonal mouse anti-human CD3 antibody and a cell selection device (such as the Miltenyi Biotec CliniMACS® cell selection device).

However, NK cells produced by such "negative selection" procedures alone do not have a high degree of purity and may be contaminated with T and B cells.

In order to reduce contamination, it is possible to obtain an NK cell preparation by direct immunomagnetic separation, for example on the basis of CD56 expression. To further reduce T cell contamination, the product may be depleted for CD3+ cells (for example using CD3 FITC and anti-FITC beads).

Prior to activation by the activating tumour cell preparation, the NK cell preparation may comprise at least 80%, at least 90%, at least 95% or at least 98% CD56+ cells.

Prior to activation by the activating tumour cell preparation, the NK cell preparation may comprise Less than 15%, less than 10%, less than 5% or less than 3% CD3+ cells.

The composition may also comprise all or a portion of the activating tumour cell preparation (i.e. activating tumour cells and/or a membrane preparation thereof) or a product thereof.

The ATCP-mediated activation may be the only activation the NK cells receive, or there may be further activation steps. The NK cells may or may not also be non-specifically activated by IL-2 (for example by incubation of the cells in medium supplemented with IL-2). Alternatively, the cells may be activated in the absence of IL-2, but IL-2 may be used for the ex vivo expansion of stimulated cells.

Medicament

The composition of the present invention may be used in medicine. For example, the composition may be used to treat or prevent cancer in a subject.

The composition comprising activated NK cells may be manufacture of a medicament for the treatment of cancer.

The composition may be administered to the subject by any suitable method known in the art, for example, intravenous infusion.

The composition may be used to treat a subject in need of same. The procedure is low-risk and particularly suitable for cancer patients for whom intensive cancer treatments are precluded (for example, elderly patients). It also provides an alternative for patients (with, for example, lymphoma, myeloma or AML) who lack a suitable donor for allogeneic stem cell transplantation.

Prior to treatment with the composition, the patient may receive some pre-treatment, for example, to de-bulk the tumour and/or immunosuppress the patient. This may be achieved, for example, by chemotherapy.

It is possible to obtain primary tumour cells from patients at time of diagnosis and to cryopreserve these as viable single cell suspensions. It is thus possible for a composition according to the invention to be tested in vitro against patient blasts. This could be done before embarking on a treatment regime, to gauge the suitability of the approach. The correlation of the results of the in vitro study and the corresponding clinical response to treatment may also be investigated.

Disease

The composition may be used to treat or prevent a disease or medical condition.

The disease may be a cancer. There are about 200 different types of cancer. List of types of cancer are available (for example, see the website for the Association of Cancer Online Resources, or the website for Cancer Research UK).

Some more common cancers include leukaemia (acute and chronic), bladder cancer, bone cancer (osteosarcoma), Bowel (colorectal cancer), brain cancer, breast cancer, cervical cancer, oesophageal cancer, Hodgkin's lymphoma, kidney cancer, liver cancer, lung cancer, mesothelioma, multiple myeloma, non-Hodgkin's lymphoma, ovarian cancer, pancreatic cancer, penile cancer, prostate cancer, skin cancer (melanoma and non-melanoma) soft tissue carcinoma, gastric cancer, testicular cancer, thyroid cancer and endometrial cancer.

The composition of the present invention may be useful to treat any cancer which is accessible to NK cells.

In particular the cancer may be a haematological malignancy, such as leukaemia (AML); Chronic lymphocytic leukemia (CLL); Lymphoma.

Myeloma is an incurable and fatal malignancy. NK activity against myeloma plasma cells is documented in vitro and enhanced NK activity against autologous myeloma cells has been shown to correlate with response to treatment with Thalidomide derivatives. Myeloma patients are generally young and fit enough to undergo autologous haematopoietic stem cell transplantation and could readily undergo a less invasive procedure such as the one provided by the present invention.

Post transplant lymphoproliferative disease (PTLD) is a serious and relatively common complication after solid organ transplantation and T cell immunotherapy is currently under trial but with little success. Therapy using NK cells activated according to the present invention therapy would be easy and safe in this group of patients.

In addition the composition may be used to treat solid tumours such as breast cancer.

The procedure is particularly suitable to treat "NK-resistant" tumours. Normal, non ATCP-stimulated NK cells can spontaneously lyse some human tumours, but many other tumours are NK-resistant. "NK-resistant" as used herein, therefore, indicates tumour cells resistant to lysis by normal, non ATCP-stimulated NK cells.

As explained above, inhibition of NK-mediated lysis is controlled by expression of specific MHC class I molecules on the target cell surface, particularly HLA-C. There are two distinct groups of HLA-C alleles with regard to NK cell recognition. Some tumours express both types of HLA-C allele, which is thought to make them resistant to NK-mediated lysis. "NK resistant" cells may, therefore express both groups of class I allele. Some leukemia/lymphoma-derived cell lines, such as Raji and Daudi express both types of HLA-C allele, making them useful models for NK-resistant tumour cells in vivo.

The invention will now be further described by way of the following non-limiting examples which further illustrate the invention, and are not intended, nor should they be interpreted to, limit the scope of the invention.

EXAMPLES

Example 1

Figure 2:
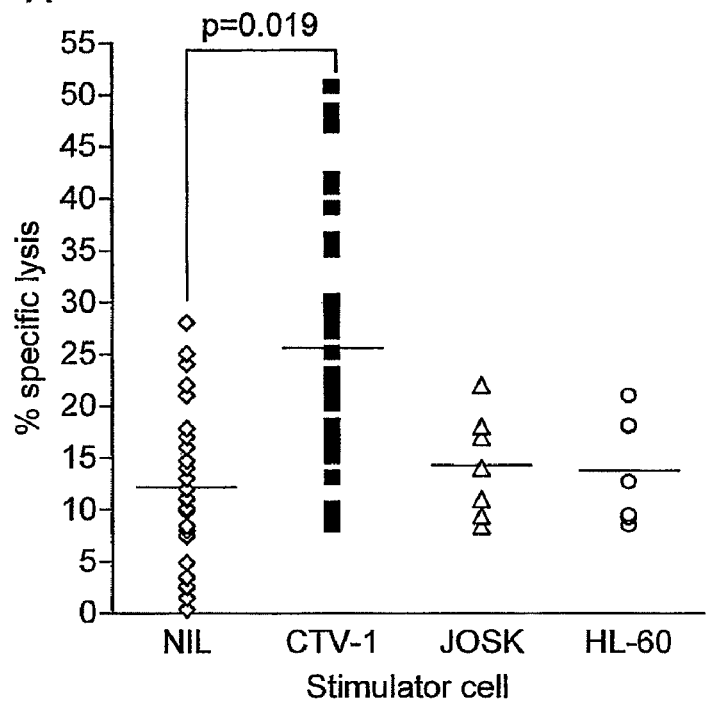
FIG. 2A is a graph showing % lysis of Raji cells when various different cell types are used as stimulator cells for NK cells.
FIG. 2B is a chart showing the effect of pre-incubation of NK cells with CTV-1 cell on % lysis various different cell types.
Figure 2:
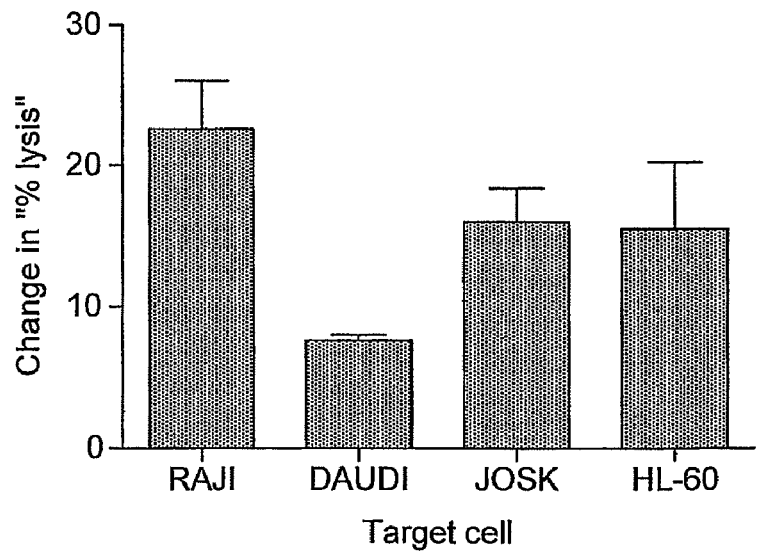
Figure 3:
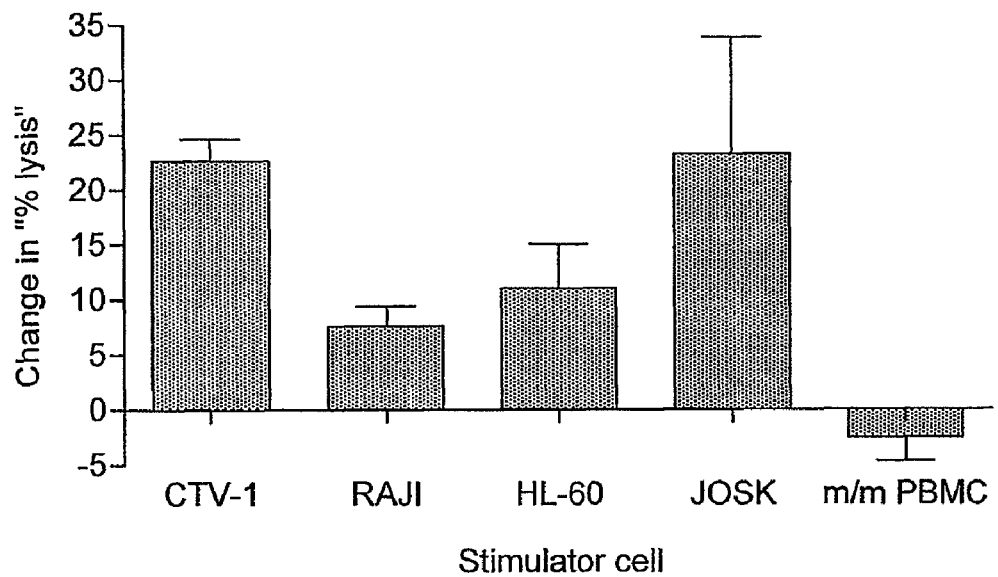
FIG. 3A is a chart showing % lysis of Raji cells when various different cell types are used as stimulator cells for NK cells.
FIG. 3B is a chart showing the effect of fixation and Brefeldin A (BFA) treatment on the capacity of CTV-1 cells to activate NK cells.
Figure 4:
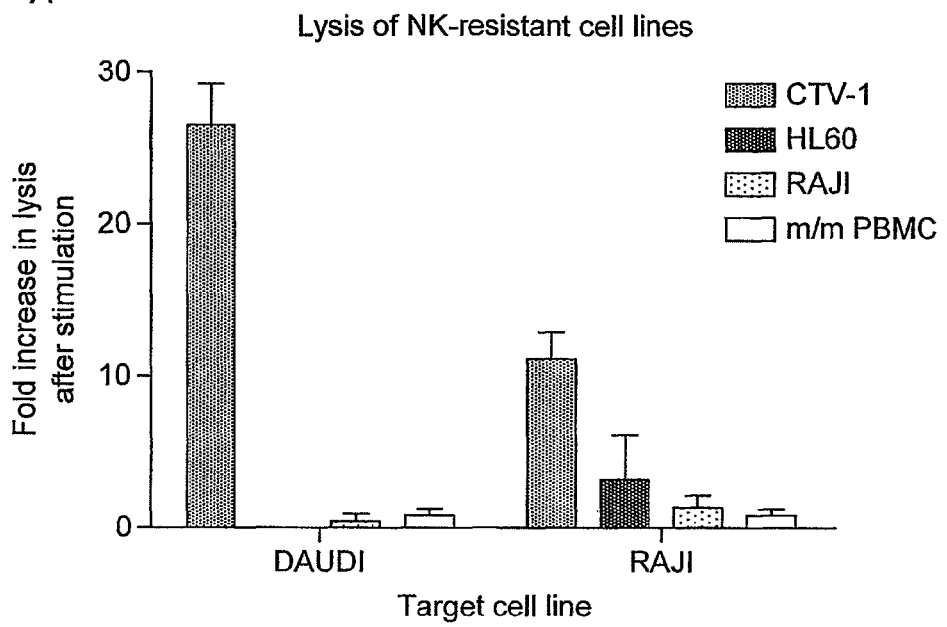
FIG. 4A is a chart showing % lysis of Raji cells and Daudi cells when various different cell types are used as stimulator cells for NK cells.
FIG. 4B is a chart showing % lysis of primary leukemia cells when various different cell types are used as stimulator cells for NK cells.
FIG. 4C is a graph showing % lysis of primary leukaemic blasts (AML and CLL) and a breast cancer cell line (MCF-7) by activated NK cells.
FIG. 4D is a graph showing % lysis of primary tumor cells from patients with breast or ovarian cancer by T-aNK cells from allogeneic normal donors.
Figure 4:
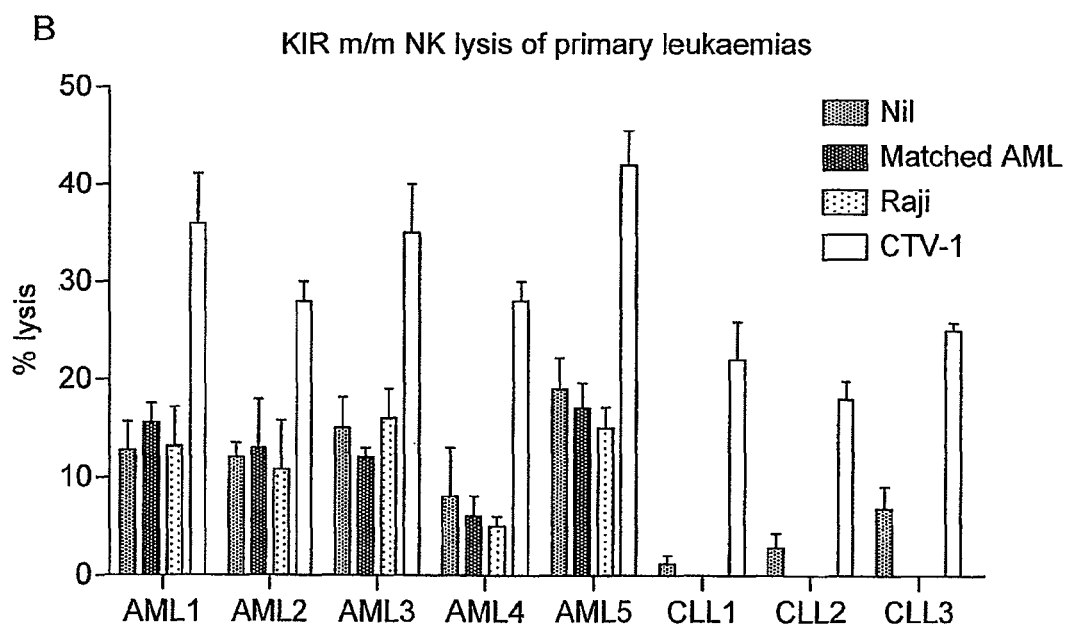
Figure 4:
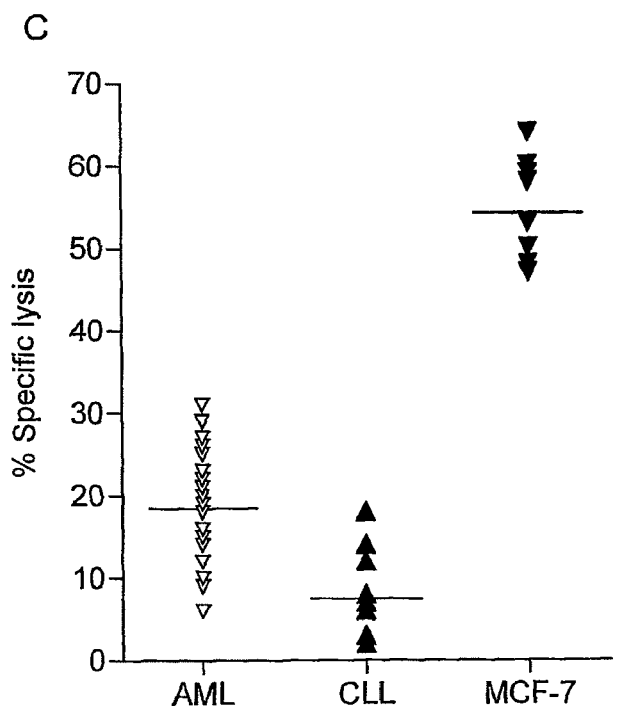
Figure 4:
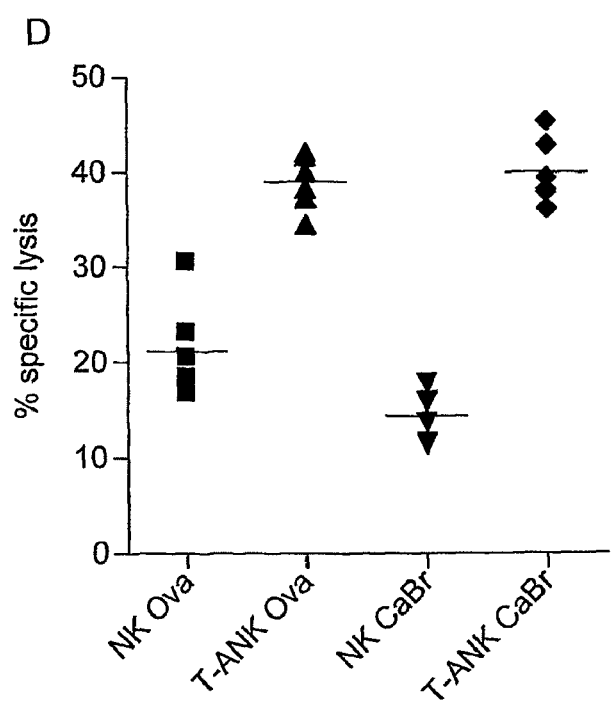

Pre-Incubation of NK Cells with Certain Tumour Cell Lines Significantly Increases the Degree of Lysis of NK-Resistant Cell Pre-incubation of normal donor NK cells with CTV-1 cells very significantly increases ($p<0.001$) the % lysis of Raji cells (FIGS. 2A, 3A and 4A). CTV-1 cells are "activating tumour cells".

Pre-incubation with HL-60 (FIGS. 2A, 3A and 4A) or Raji cells (FIGS. 3A and 4A) are less effective or ineffective in activating the NK cells to lyse Raji cells. Pre-incubation with allogeneic HLA-KIR mismatched normal PBMC does not induce NK activation (FIG. 4A). In these experiments, the tumour cells express normal levels of MHC class I antigens as do the Daudi and Raji cell lines. Daudi and Raji cells both express HLA-C molecules which ligate both class 1 and class 2 KIRs.

Pre-incubation with CTV-1 causes an increase in the degree of lysis of various tumour cell-lines, such as Raji, Daudi, JOSK and HL-60 (FIG. 2B).

Example 2

Investigating the Requirements for NK Cell Activation

The effect of fixation and Brefeldin A (BFA) on NK activation by CTV-1 cells is investigated using multiple normal donors. As shown in FIG. 3B, induction of NK activation requires contact with the tumour cell line although does not require secretion of a cytokine since fixation of the tumour cells does not abrogate the response. The NK cells do need to synthesise a protein in response to the tumour cell ligation as addition of Brefeldin A during the pre-incubation prevents induction of the activated state.

Example 3

Investigation of the Effect of KIR Ligation

Figure 6:
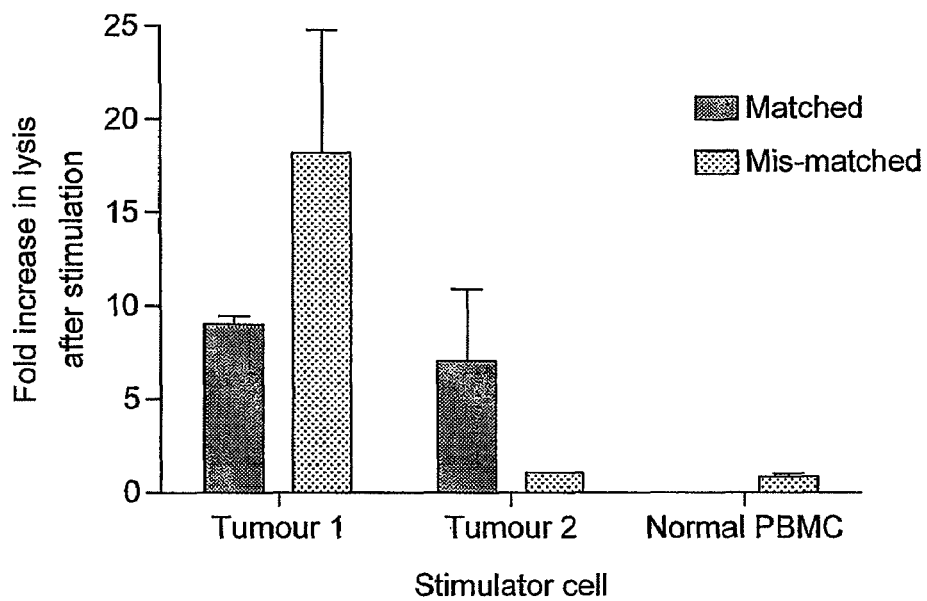
FIG. 6A is a chart comparing the effect of using HLA-KIR mismatched versus HLA-KIR matched activating tumour cell lines
FIG. 6B is a graph showing the % lysis of Raji targets by NK cells activated by either KIR-ligand matched and mismatched CTV-1 cells.
Figure 6:
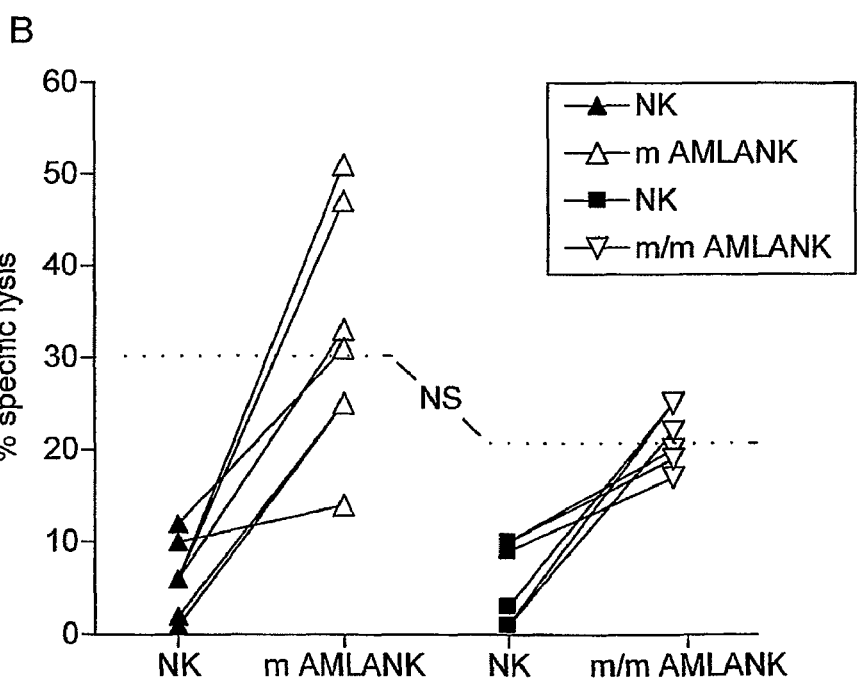

In order to investigate the effect of KIR ligation during the stimulation phase, the use of HLA-KIR matched and mismatched stimulating tumour cell lines is compared on the stimulation of NK cells to lyse Raji cells. The stimulating tumour cell lines need not be HLA-KIR mismatched to the donor NK cells although it appears that the threshold for NK activation by the tumour cell line may be lower in the absence of KIR ligation (FIG. 6A).

Figure 7:
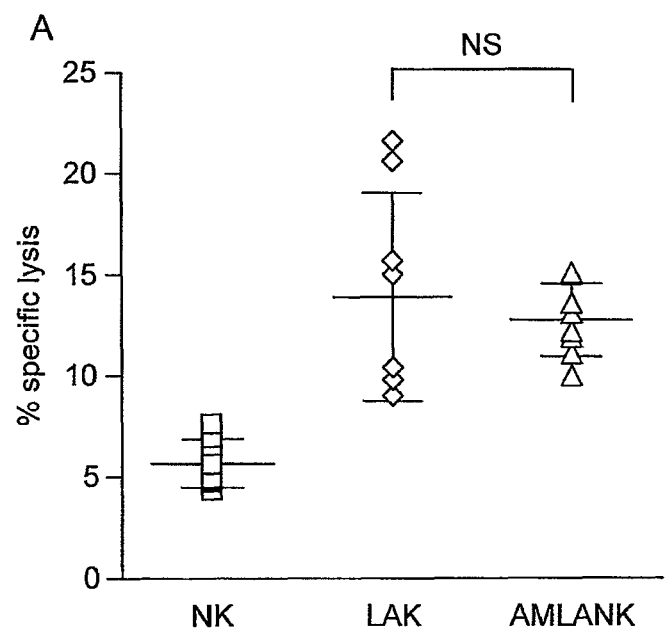
FIG. 7A is a comparing lysis by ATCP-activated and IL-2 stimulated NK cells.
FIG. 7B is a graph showing % lysis of leukaemic blasts at different E:T ratios.
FIGS. 7C and 7D are graphs showing the effect of KIR mismatching on CTV-1 induced NK activation (C) CD56+/CD3− NK cells are incubated overnight in medium alone (open bars), with irradiated CTV-1 cells (shaded bars), or with CTV-1 cell lysate (black bars) and phenotyped for expression of KIRs and CD69 (bars show mean+/−sd). (D) Resting NK cells are flow sorted from 3 normal donors into two populations of those co-expressing CD158a and CD158e1 and those lacking both molecules. These are stimulated overnight with CTV-1 cell lysates and their cytolytic activity tested against RAJI cells in a 4-hour assay (bars show mean+/−sd).
Figure 7:
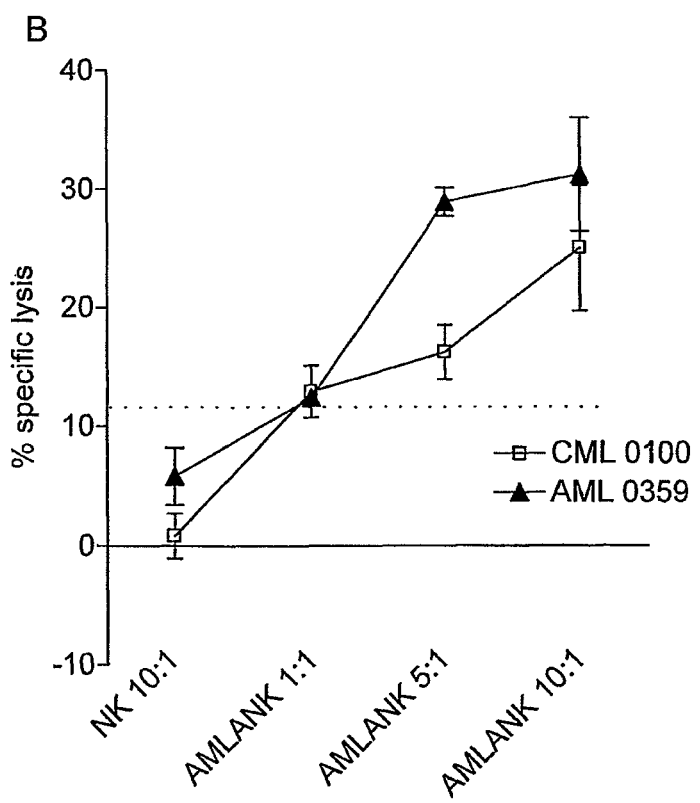
Figure 7:
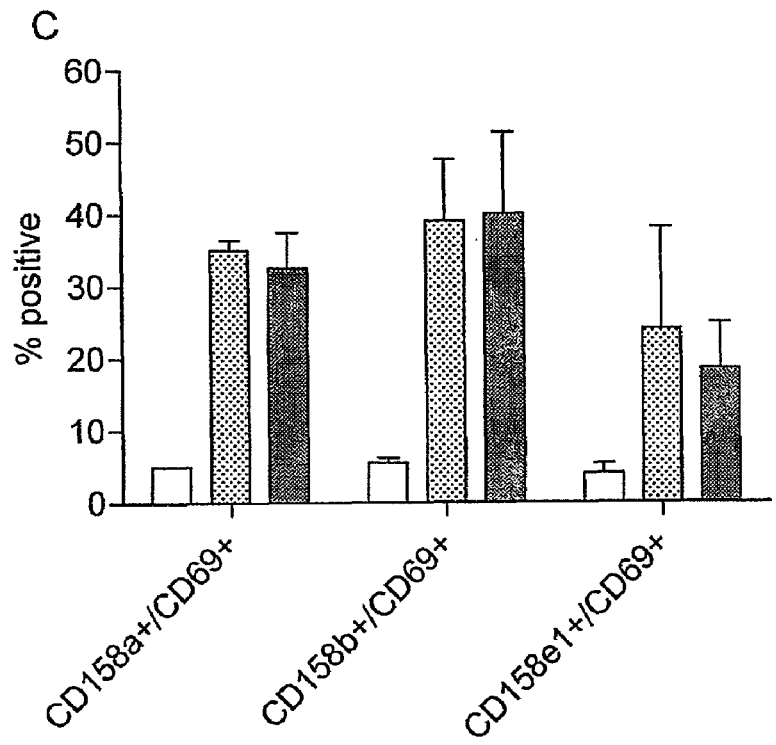
Figure 7:
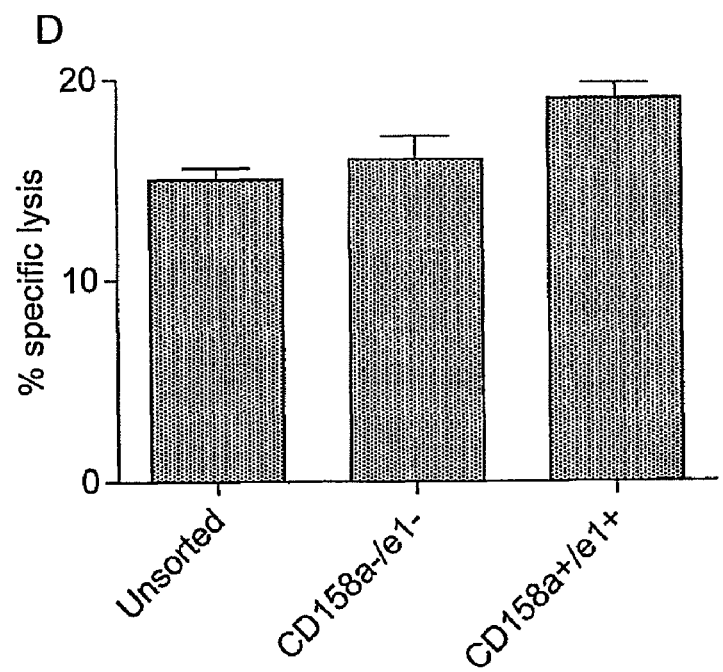

In another experiment, purified NK cells from normal donors are selected on the basis of their HLA-A, -B and -C type as KIR-ligand matched or mis-matched with CTV-1 cells. CTV-1 cells are HLA-C type 2 homozygous and express HLA-Bw4 alleles. They thus ligate KIR2DL1 and KIR3DL1 on NK cells. NK:CTV-1 co-cultures are established with NK cells expressing KIR2DL1, expressing KIR2DL1 and KIR3DL1 and with cells expressing only KIR2DL2/3, the ligand for which is missing from CTV-1 stimulator cells. It is thus possible to evaluate the contribution of "missing self" to the NK activation step. AMLANK (AML-activated NK cells) are generated by CTV-1 from both HLA-/KIR matched and mismatched donors and there is no significant difference in the degree of specific lysis although the AMLANK from matched donors show greater heterogeneity (FIG. 6B). The degree of lysis is equivalent to that obtained by non-specific activation with IL-2 (FIG. 7A).

The KIR phenotype of peripheral blood NK cells is not completely restricted by the HLA of the individual and it is common for NK cells to lack appropriate KIRs for self MHC and even to express KIRs specific for HLA alleles absent from the individual. In another experiment, NK cells from normal donors are co-incubated overnight with CTV-1 and phenotyped for expression of KIR and of CD69. It is readily apparent that CTV-1 induced NK activation is not restricted to KIR mismatched NK cells since cells expressing CD158a and CD158e1 show equivalent levels of activation as NK cells from the same donors which lack CD158a or CD158e1 but express CD158b, the ligand for which is absent from CTV-1 (FIG. 7c). To more precisely investigate the role of KIR in the CTV-1 mediated activation and in the lysis of Raji, NK cells are phenotyped and selected on their KIR compatibility to the HLA of the CTV-1 stimulator cells by flow cytometric sorting. Flow sorted NK cell subsets are either incubated directly with CTV-1 cells or are incubated overnight so that the anti-KIR antibody is shed from the NK cell and cannot block KIR:HLA interaction. In both cases the NK cells expressing CD158a and CD158e1 show equivalent lysis of Raji cells compared to CD158a/e1-ve NK from the same donors (FIG. 7d).

Example 4

Lysis of Primary Leukemias

In addition to their capacity to lyse NK-resistant tumour cell lines, it is also shown that CTV-1 activated NK-cells have a greatly increased capacity to lyse primary leukemia cells, when compared to NK cells pre-incubated with HLA-KIR matched AML cells or Raji cells (FIGS. 4B and C).

AMLANK cells from allogeneic donors are capable of lysis of primary AML cells of all FAB types (FIG. 4C). These cells also lyse primary CLL cells at an effector:target cell ratio of 1:1 although the level of killing is low. It was notable that the relatively NK-resistant breast cancer cell line, MCF-7, is extremely susceptible to AMLANK cells (Example 5) as are primary tumor cells isolated from ressected tissue from patients with breast cancer and ovarian cancer (FIG. 4D).

The lack of requirement for HLA mismatch is confirmed in a study of two HLA-identical donors and their respective siblings with leukaemia. AMLANK cells from the HLA-identical sibling donor for Patient 0100 effectively lyse cryopreserved CML blasts obtained from the patient at disease presentation. This lysis was apparent at an E:T ratio of 1:1 and was increased at increasing E:T ratios. In contrast, NK cells from the same donor were unable to lyse the CML blasts even at the highest E:T ratio of 10:1. The same was observed using AMLANK cells from an HLA-identical sibling donor for patient 0359 who presented with AML M2 and from whom presentation blasts had been cryopreserved.

Example 5

Lysis of CaBr Cell Lines

The breast cancer cell line MCF-7 was extremely susceptible to AMLANK lysis at an E:T ratio of 5:1 after a four hour incubation period (FIG. 4C).

Example 6

Investigation of the Effect on Normal Haematopoietic Cells

Figure 5:
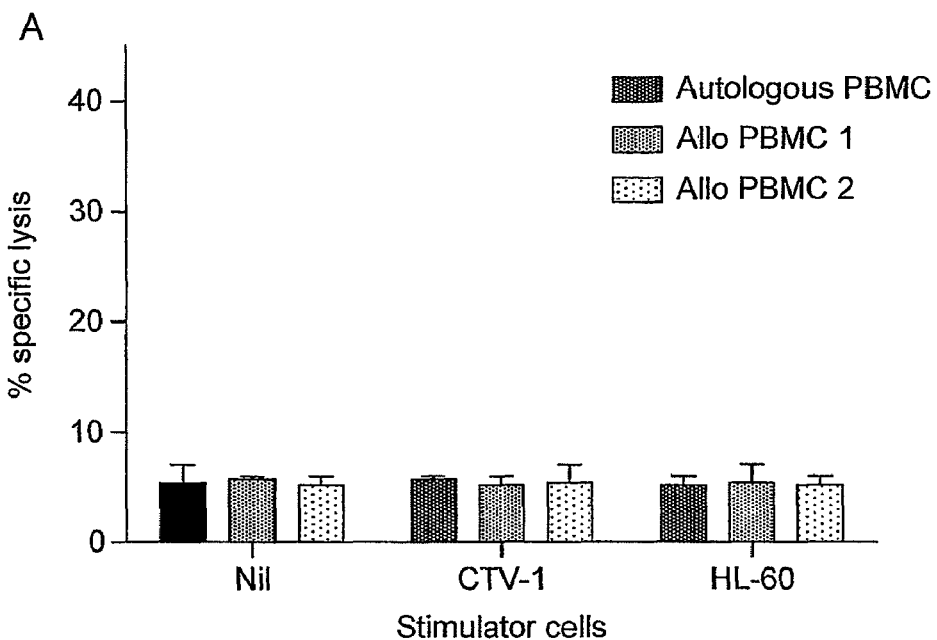
FIG. 5A is a chart showing the effect of stimulated NK cells on KIR-matched (autologous) or KIR mismatched (haplo 1 or haplo 2) normal PBMC.
FIG. 5B is a graph to show lysis by activated NK cells from normal donors on normal PBMC from the same donor (autologous) and KIR-mismatched normal donors (allogeneic).
FIG. 5C is a chart showing the effect of activated NK cells on in vitro haemotopoiesis of normal donor BMMC
Figure 5:
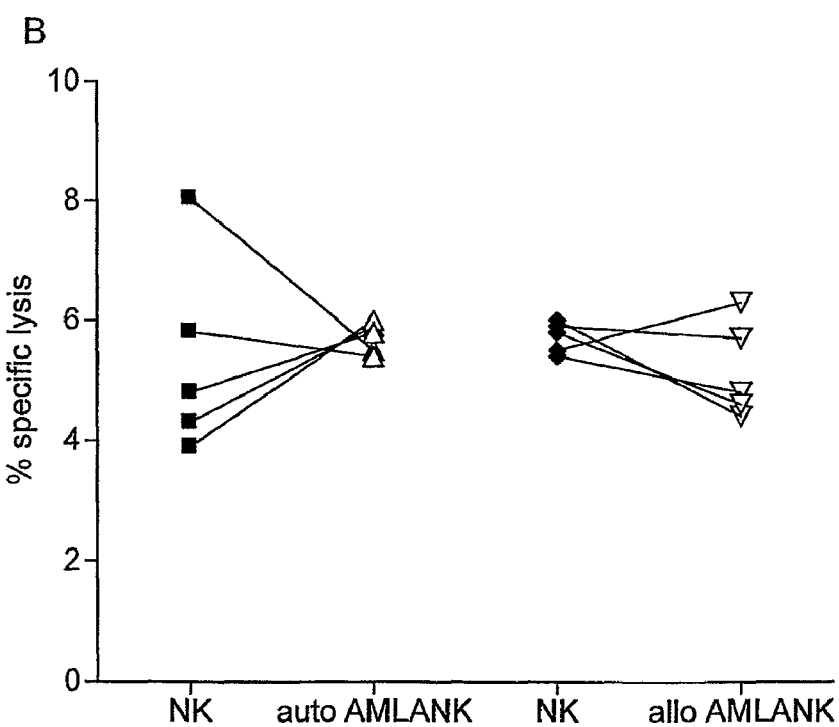
Figure 5:
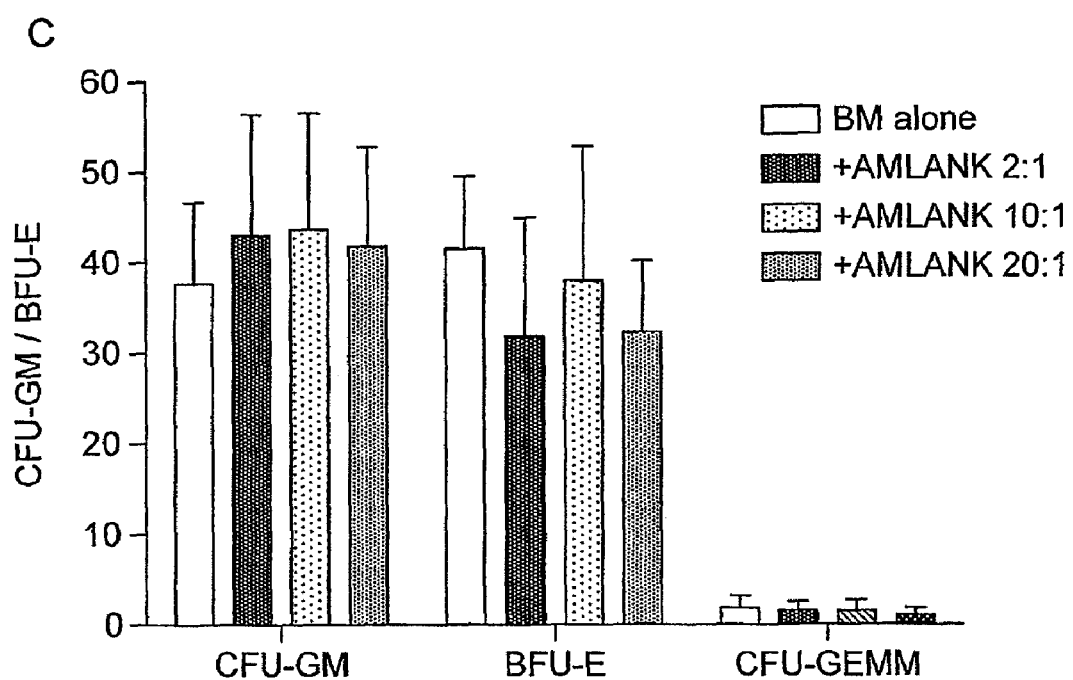

Stimulation of haplo-mismatched normal donor NK cells with the two tumour cell lines does not initiate lytic responses to KIR-matched (autologous) or KIR mismatched (haplo 1 or haplo 2) normal PBMC (FIG. 5A).

To investigate the tumour-specificity of allogeneic AMLANK cells, NK cells are isolated from normal donors and either activated with CTV-1 cells overnight or maintained in media. These AMLANK cells are then compared with matched NK cells with respect to lysis of normal autologous and allogeneic PBMC. Neither NK nor AMLANK cells lyse autologous PBMC nor do they lyse PBMC from HLA-C mismatched normal donors (FIG. 5B). To determine the likelihood of bone marrow suppression by AMLANK cells hematopoietic colony forming assays are established with bone marrow from 5 normal donors and added AMLANK from HLA-C mismatched donors at increasing ratios. CFU-GM, BFU-E and CFU-GEMM are not affected by co-incubation with HLA-mismatched AMLANK (FIG. 5C).

Example 7

Investigation of Lysis by AMLANK Cells

Comparison of AMLANK cells with resting NK and with IL-2 stimulated NK cells (lymphokine activated killer—LAK) from the same donors shows equivalent lysis of Raji (FIG. 7A).

In contrast to resting NK cells at a high E:T ratio (10:1), AMLANK cells are capable of detectable lysis of the presentation leukaemic blasts even at a 1:1 ratio (FIG. 7B). The dashed line (in FIG. 7B) represents the degree of specific lysis of AML blasts which we have previously reported as being associated with continued remission in AML patients after chemotherapy (Lowdell et al (2002) Br. J. Haematol. 117: 821-7).

Example 8

Investigating the Significance of CD69

Figure 8:
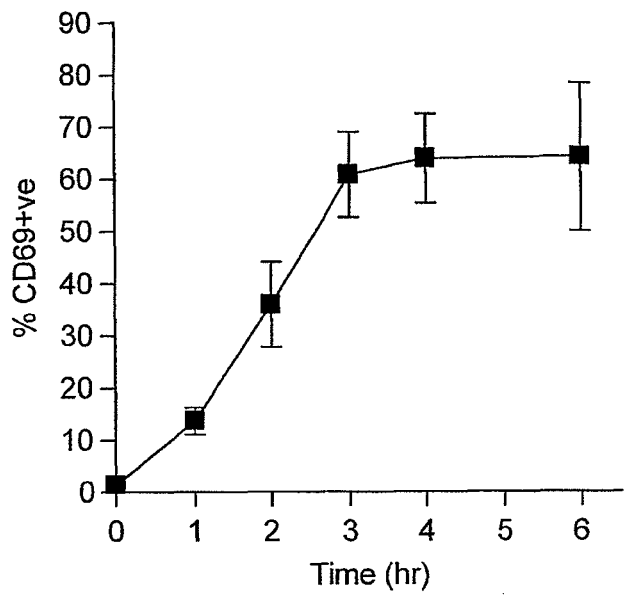
FIG. 8A is a graph showing the proportion of CD69+ve cells within the CD56+ NK fraction of CTV-1-activated NK cells.
FIG. 8B is a chart showing the effect of incubation with CTV-1 on the expression of a panel of ligands by NK cells.
Figure 8:
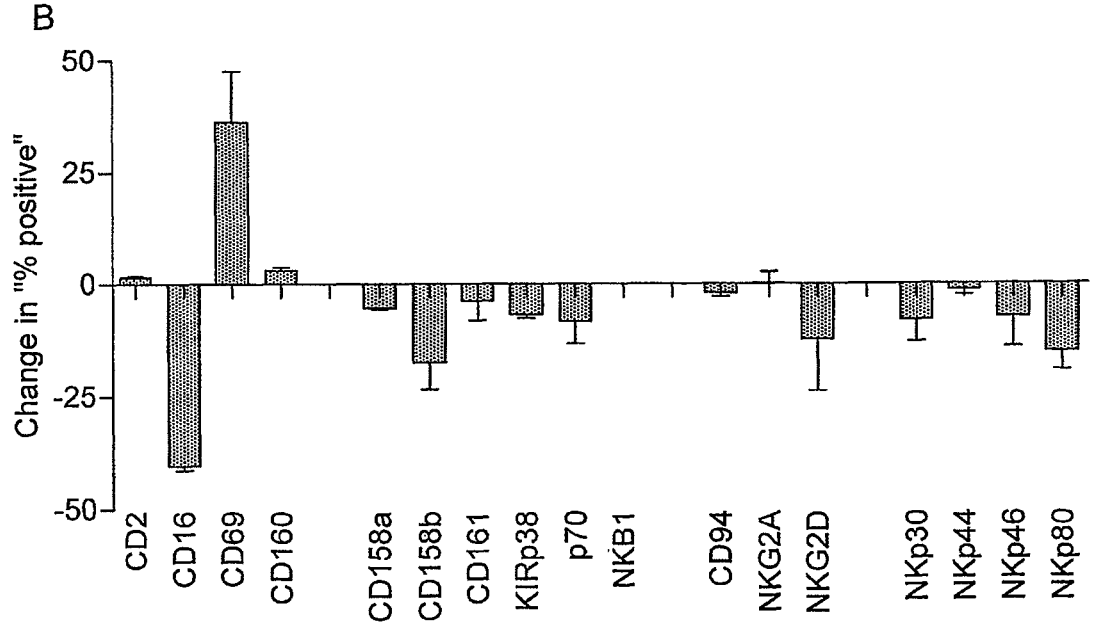

Co-incubation of normal donor NK cells with equal numbers of irradiated CTV-1 cells induces rapid and sustained expression of CD69 on the NK cells (FIG. 8A). Purified NK cells are mixed with an equivalent number of irradiated CTV-1 cells which have been labelled with PKH-26. Aliquots are removed at the time points indicated and labelled with anti-CD56 FITC and anti-CD69 APC, washed and analysed by flow cytometry. CTV-1 cells are excluded from the analysis on the basis of forward angle light scatter (FSC) and PKH-26 expression and NK cells are positively included on the basis of FSC and CD56 expression. Results are presented from 10 normal donors and expressed as the proportion of CD69+ve cells within the CD56+ NK fraction.

When normal donor NK cells (n=10) are incubated with or without irradiated CTV-1 overnight, matched pair comparisons of the expression of a range of candidate activating and inhibitory ligands by flow cytometry shows there is a significant increase in CD69 expression (p<0.001) but no increase in any of the other stimulatory ligands studied (FIG. 8B). Expression of CD16 is reduced. CD69 upregulation is blocked in the presence of Brefeldin A (data not shown).

Figure 9:
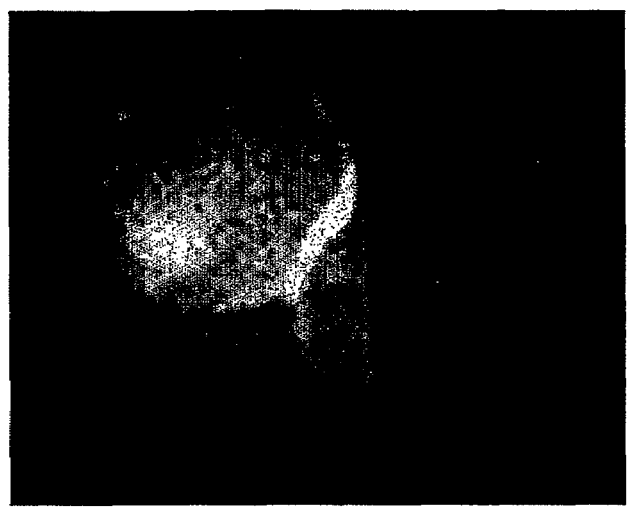
FIG. 9A is a confocal microscopy photograph showing conjugate formation between activated NK cells and Raji cells and capping of CD69 at the immune synapse.
FIG. 9B is a gel photograph showing HPLC fractionation of recombinant human CD69 re-folded protein supernatant.
FIG. 9C is a panel of histograms showing flow cytometric analysis of labelled Raji cells after contact with nano-particles coated with HPLC fractions from rCD69 supernatant.
FIG. 9D is a confocal microscopy photograph of labelled Raji cells after contact with nano-particles coated with an rCD69-positive HPLC fraction.
FIG. 9E is a confocal microscopy photograph of labelled normal B cells after contact with nano-particles coated with an rCD69-positive HPLC fraction.
FIG. 9F is a graph showing % lysis of Raji cells following pre-incubation with 260 μg-1 mg of rCD69 HPLC fractions (in the absence of nano-particles).
FIG. 9G is a graph to show flow cytometric analysis of Raji cells after labelling with nanoparticles coated with rCD69 (shaded histogram) or denatured rCD69 (open histogram).
FIG. 9H is a graph to show flow cytometric analysis of K562 cells after labelling with nanoparticles coated with rCD69 (shaded histogram) or denatured rCD69 (open histogram).
FIG. 9I is a graph to show flow cytometric analysis of normal T cells cells after labelling with nanoparticles coated with rCD69 (shaded histogram) or denatured rCD69 (open histogram).
FIG. 9J is a graph to show flow cytometric analysis of normal B cells after labelling with nanoparticles coated with rCD69 (shaded histogram) or denatured rCD69 (open histogram).
FIG. 9K is a graph to show flow cytometric analysis of normal NK cells after labelling with nanoparticles coated with rCD69 (shaded histogram) or denatured rCD69 (open histogram).
FIG. 9L is a graph to show the relative fluorescence intensity observed with different cell lines.
FIG. 9M is a chart to show T-aNK mediated lysis of RAJI cells in the presence of rCD69 at two concentrations
FIG. 9N is a chart to compare T-aNK mediated RAJI cell lysis in the presence of rCD69, denatured rCD69 or BSA.
FIG. 9O is a chart to show the effect of rCD69 on lysis of K562 by resting NK cells or T-aNK cells
Figure 9:
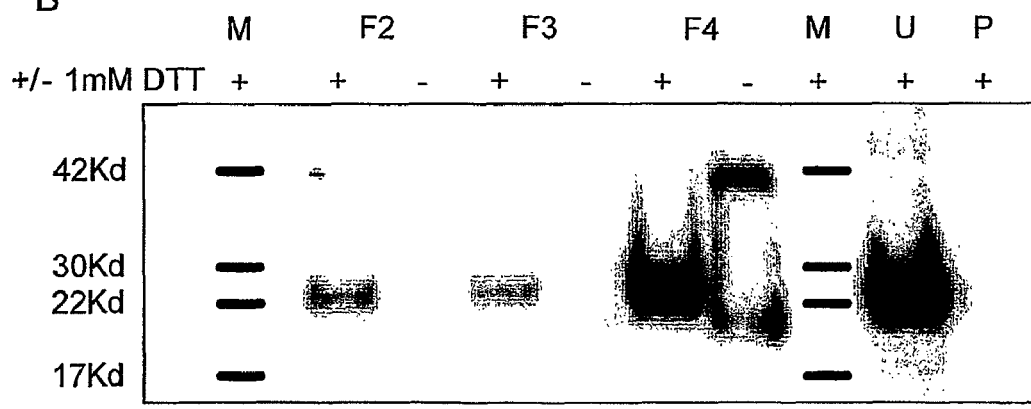
Figure 9:
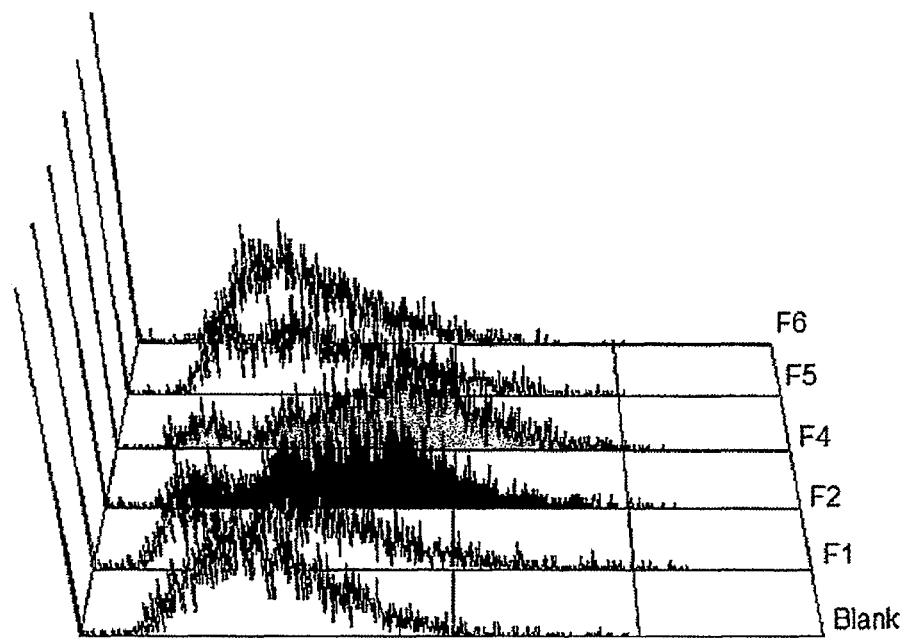
Figure 9:
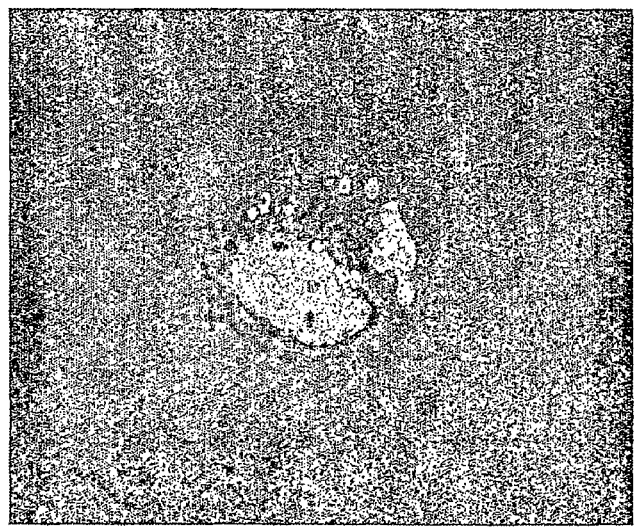
Figure 9:
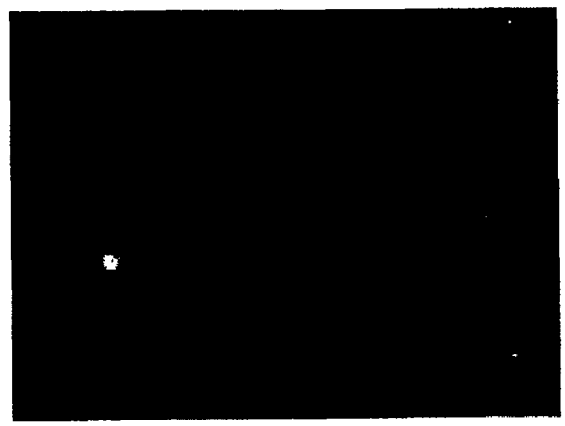
Figure 9:
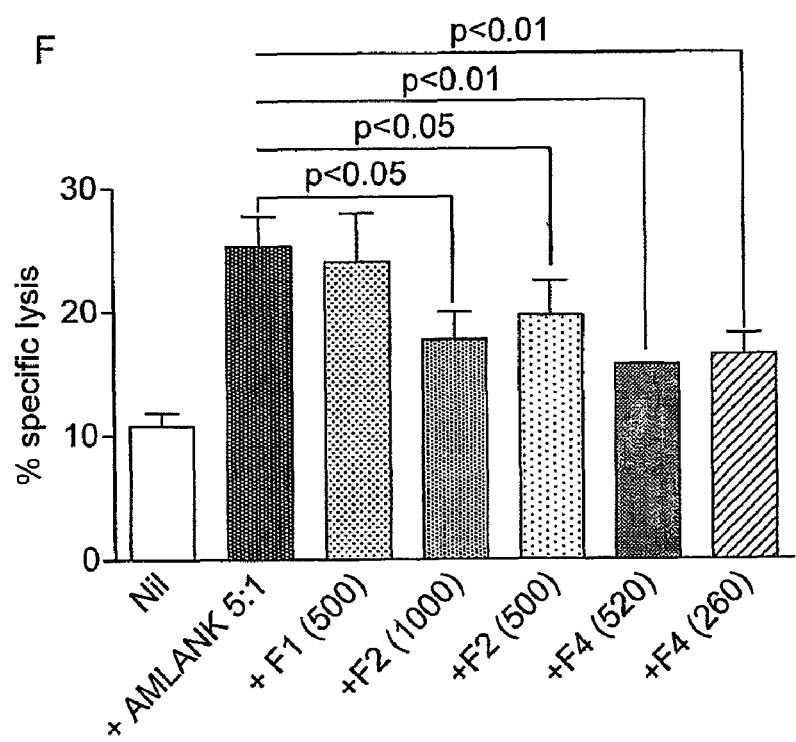
Figure 9:
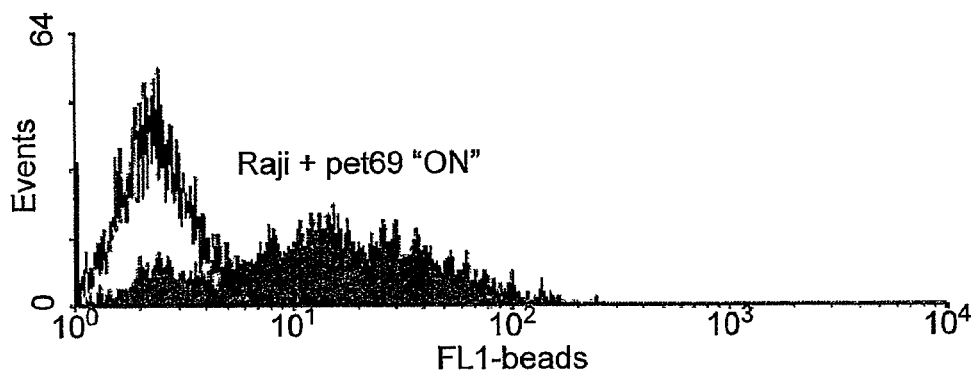
Figure 9:
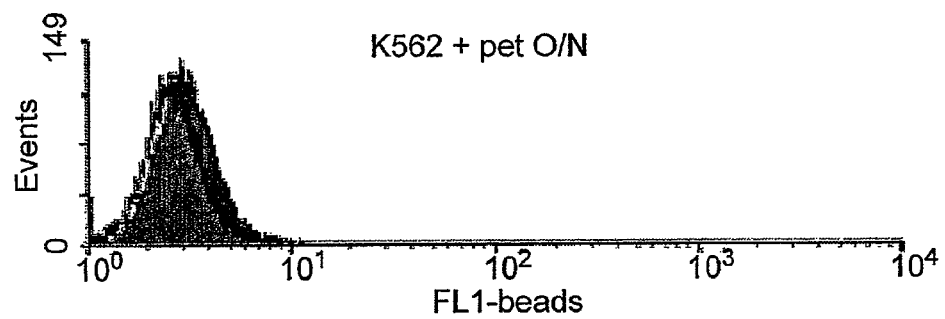
Figure 9:
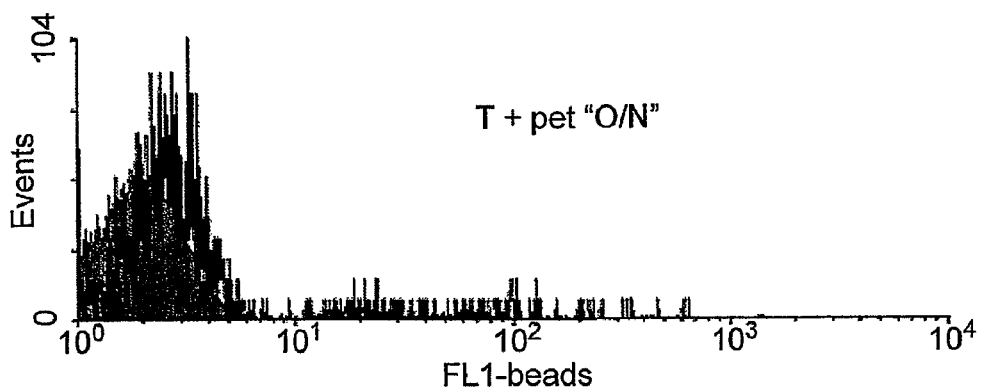
Figure 9:
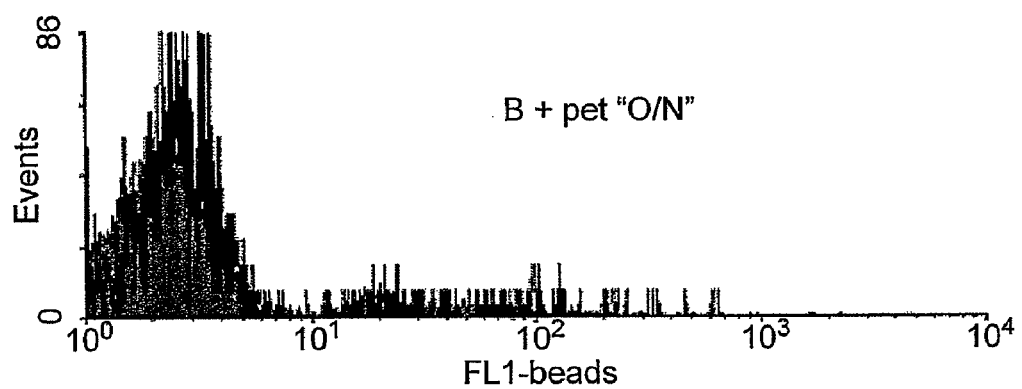
Figure 9:
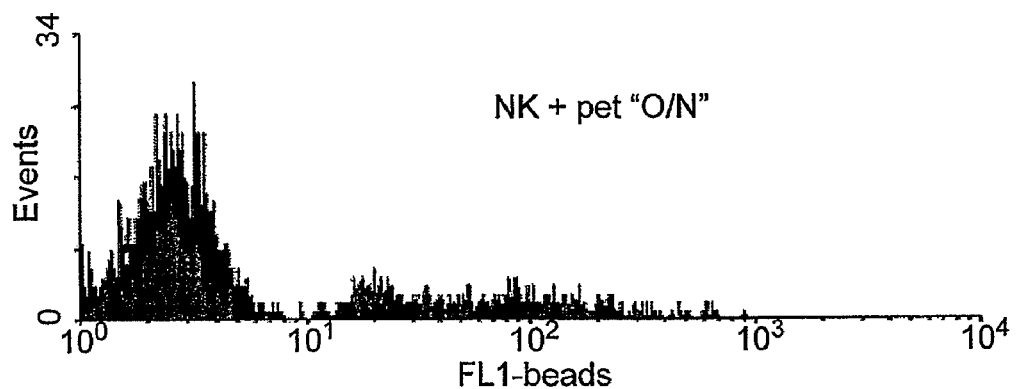
Figure 9:
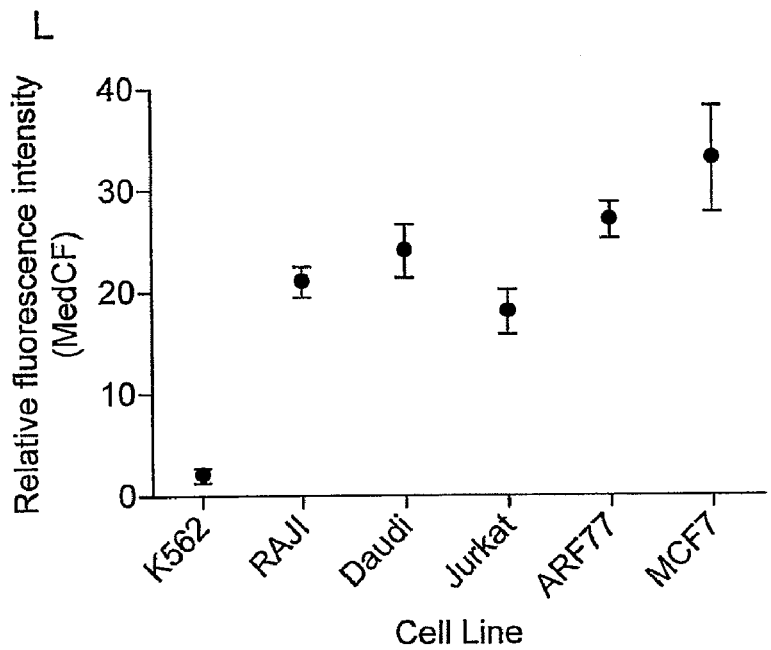
Figure 9:
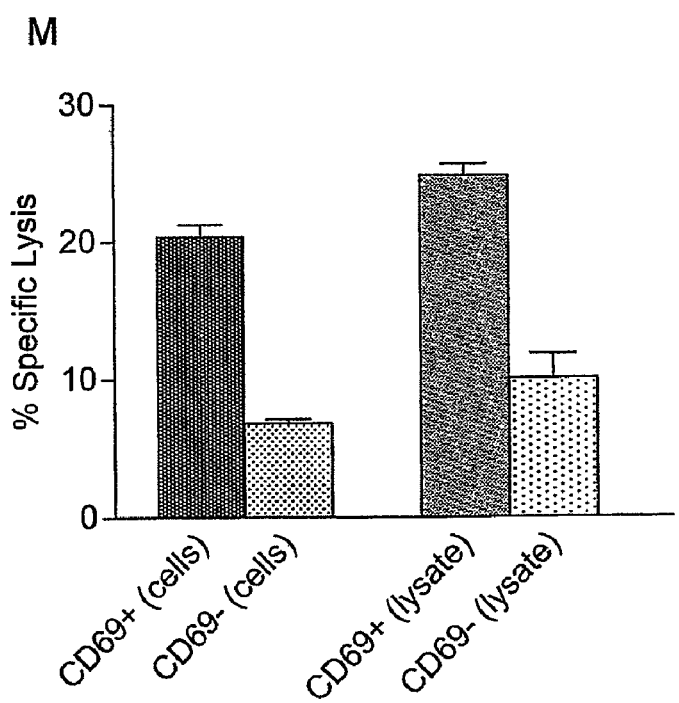
Figure 9:
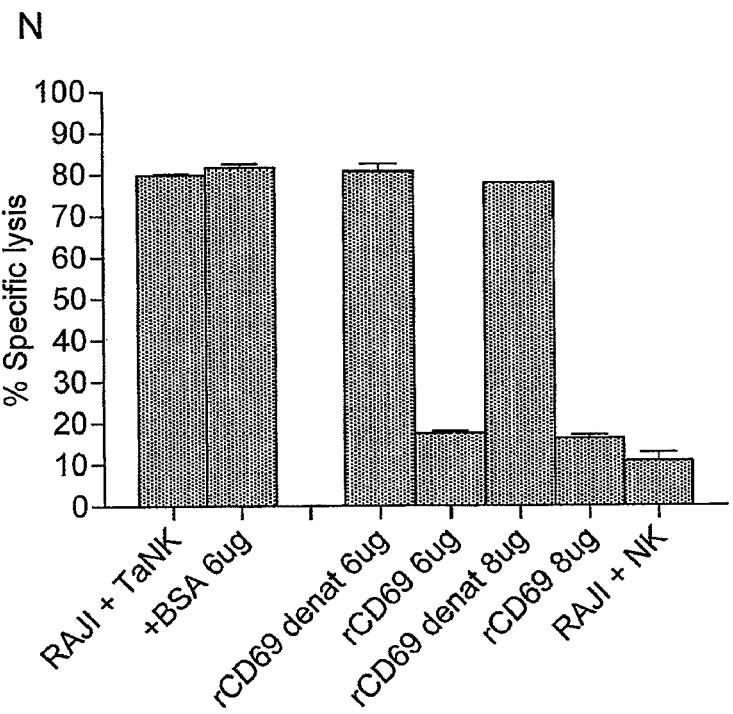
Figure 9:
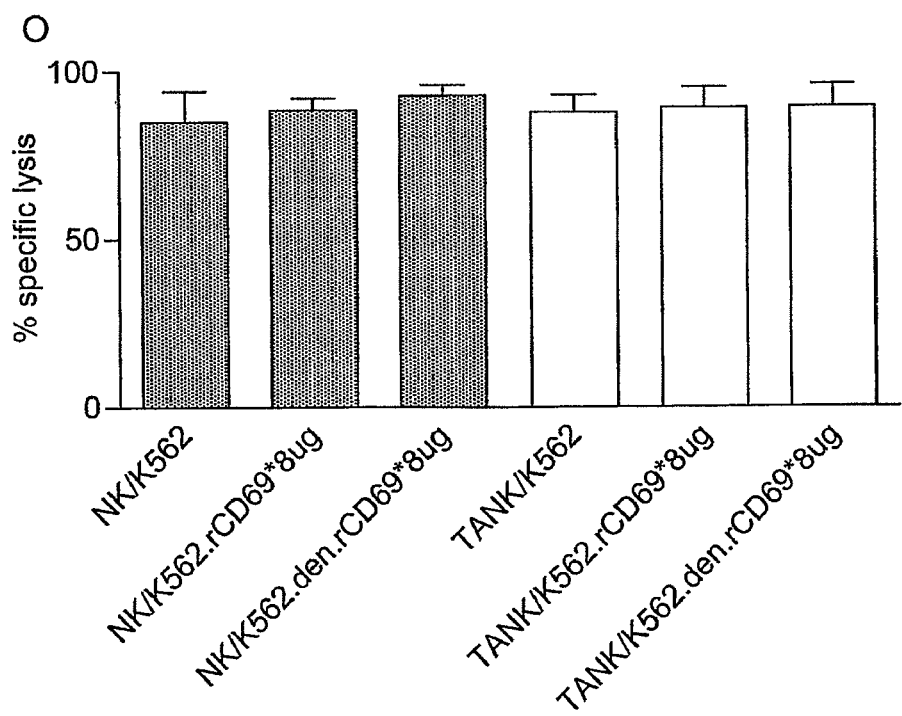

AMLANK cells co-incubated with Raji cells at a 1:1 E:T ratio show conjugate formation at 60 min by confocal microscopy and capping of CD69 at the immune synapse. FIG. 9A shows a single AMLANK cell from a normal donor conjugated to a single Raji cell. The conjugate is labelled with anti-CD69 FITC and Dapi as the nuclear stain. Recombinant human CD69 is generated as described and the re-folded protein supernatant fractionated by HPLC. Fractions F2 and F3 contain monomeric rCD69 when assessed by Western blot under reducing conditions. Fraction 4 contains considerably higher concentrations of rCD69 which is detectable as a monomer in the presence of DTT and as both a monomer and a dimer in non-reducing conditions (FIG. 9B). rCD69 is absent from the parental bacterial strain (lane P) and from all other HPLC fractions tested (data not shown). Flow cytometric analysis of labelled Raji cells shows positive binding only with nano-particles coated with HPLC fractions containing rCD69 (shaded histograms in FIG. 9C). This binding is confirmed by confocal microscopy (D) and flow cytometry (G). In contrast to the malignant B cell line, normal B cells do not bind the beads (E). CD69L expression is also absent from NK sensitive K562 cells (FIG. 9H), normal T cells (FIG. 9I), normal B cells (FIG. 9J) and normal NK cells (FIG. 9K) from all healthy donors (n=3). CD69L expression was also detected on other cell lines susceptible to T-ANK mediated lysis including Daudi cells, Jurkat cells, MCF-7 cells and ARH77 cells (table 1).

TABLE 1

Tissue distribution of CD69L expression

| Cell Line | Cell type | CD69L expression |
|---|---|---|
| Normal T cells | | Negative |
| Normal B cells | | Negative |
| Normal NK cells | | Negative |
| RAJI | Burkitt's Lymphoma | Positive |
| Daudi | Burkitt's Lymphoma | Positive |
| K562 | Erythroleukemia | Negative |
| ARH77 | Myeloma | Positive |
| Jurkat | T cell lymphoma | Positive |
| MCF-7 | Metastatic breast tumor | Positive |

Pre-incubation of Raji cells with 260 µg-1 mg of fractions 2 or 4 (in the absence of nano-particles) significantly inhibits AMLANK lysis of Raji cells in contrast to pre-incubation with fraction 1 which contained no rCD69 (F).

To summarise, the present inventors have previously shown that CD69 expressed on the activated NK cell caps at the immunological synapse with an autologous AML cell (Lowdell et al (2002) as above) and have now confirmed this at the synapse between AMLANK and Raji cell (FIG. 9A).

Without wishing to be bound by theory, these findings imply that CD69 ligand (CD69L) is expressed on AMLANK-sensitive tumour cells. CD69L is currently unknown.

CD69 is Critical for Tumor-Restricted Killing by T-ANKs

To establish the role of the CD69:CD69L interaction in T-ANK activity the CD69+ T-ANK cells are sorted after CTV-1 stimulation from the CD69−ve cells prior to a RAJI lysis assay. The CD69+ve fraction mediates 83.7% of the activity of unfractionated T-ANK cells whereas the CD69−ve NK cells show 5.5% (FIG. 9M). The critical role of CD69 in T-ANK triggering is confirmed by the inhibition of RAJI cell lysis in the presence of rCD69. Pre-incubation of RAJI cells with rCD69 significantly reduces the degree of RAJI cell lysis almost to the level of lysis by resting NK cells. This effect is not observed when RAJI cells were pre-incubated with BSA or heat denatured rCD69 (FIG. 9N).

As expected, rCD69 does not block lysis of K562 either by resting NK cells or by T-ANK cells (FIG. 9O).

The resistance of normal haematopoietic cells to lysis by AMLANK cells, even in the absence of relevant KIR-ligating HLA, implied that the tumour cells express a tumour-restricted ligand which is responsible for NK lysis. The lack of AMLANK generation in the presence of Brefeldin A confirmed that the signalling molecule for AMLANK-mediated lysis was newly synthesised upon co-incubation with the stimulatory tumour cells. Of the known NK triggering molecules, only CD69 is upregulated during the pre-incubation.

CD69 is a homodimeric glycoprotein expressed on many haematopoietic cells upon activation. On human NK cells it has been shown to initiate tumour cell lysis when ligated (Demanet et al (2004) Blood 103:3122-3130) although murine data imply that CD69 ligation is inhibitory to NK-mediated lysis since CD69 KO mice show enhanced anti-tumor activity (Esplugues et al (2003) J. Exp. Med. 197:1093-1106) and monoclonal antibody blockade of CD69 on murine NK cells increases their lytic activity (Esplugues et al (2005) 105:4399-4406). By producing a recombinant dimeric human CD69 molecule the inventors have shown that tumour cells express the ligand for CD69 which is absent from normal haematopoietic cells. Furthermore, blocking experiments with CD69L confirm that CD69 on activated NK cell is the predominant trigger molecule for AMLANK cytotoxicity. This is supported by the evidence that AMLANK:Raji cell conjugation leads to Syk activation within the AMLANK cells (data not shown), a phenomenon known to be associated with CD69-mediated signalling (Pisegna et al (2002) 169:68-74).

Materials and Methods for Examples 1-8

Cell Lines and Primary Cells

All cell lines are obtained from the American Typed Cell Collection (ATCC) and maintained in continuous suspension culture in "Complete Media" (CM) consisting of RPMI 1640 supplemented with 10% FCS, 100 i.u. penicillin and 100 i.u. streptomycin (all supplied by Gibco, Paisley, Scotland). Fresh peripheral blood mononuclear cells (PBMCs) are isolated from heparinized venous blood from normal healthy donors by discontinuous density gradient separation (Lymphoprep, Nycomed, UK) and used within four hours of venesection.

Immunophenotyping

To analyze cell surface antigen expression, $10^5$ cells in 10 µL HBSS are incubated with fluorochrome conjugated MAbs at the manufacturers' recommended concentration for 15 mins at room temperature. After washing the cells are analysed by flow cytometry (FACS Calibur with CellQuest software, Becton Dickinson, UK). Forward and side light scatter characteristics are used to gate on the viable lymphocyte population before acquisition of at least 10 000 cells from each sample. All fluorochrome conjugated mAbs are purchased from BD (Cowley, UK) or Beckman Coulter (High Wycombe, UK).

Purification of Human NK Cells and Target Cells

Fresh heparinised peripheral blood samples are obtained after informed consent from normal healthy donors, patients with acute and chronic leukemias at diagnosis (Table 1) and from two HLA-identical PBSC sibling donors of patients selected for allogeneic stem cell transplant and who had donated bone marrow samples at time of their disease presentation; the leukemic blasts from which had been cryopreserved in multiple aliquots.

Mononuclear cells (PBMCs) are isolated from venous blood by discontinuous density gradient separation (Lymphoprep, Nycomed, UK) and typed for HLA class I A and B alleles by low resolution techniques and HLA-Cw to high resolution. CD56+CD3− cells are purified from PBMCs by direct immunomagnetic separation with CD56 Multisort kit (Miltenyi Biotec, Germany) and subsequent depletion with CD3 FITC and anti-FITC beads. All selected cells are confirmed as >98% CD56+ and <3% CD3+ and resuspended in CM.

TABLE 2

Patient characteristics

| Identifier | Diagnosis | Age | Gender |
|---|---|---|---|
| AML0191 | AML M0 | 31 | M |
| AML0231 | AML M2 | 42 | M |
| AML0258 | AML M4 | 35 | M |
| AML0273 | AML M2 | 22 | M |
| AML0302 | AML M4eo | 28 | F |
| AML0306 | AML M6 | 48 | M |
| AML0314 | AML M3 | 40 | M |
| AML0317 | AML M7 | 24 | M |
| AML0359 | AML M4 | 19 | M |
| CLL727 | | | |
| CLL728 | | | |
| CLL729 | | | |
| CLL730 | | | |
| CML0100 | Chronic phase | 52 | F |

Tumour-Specific Activation of NK Cells

Freshly isolated NK cells are suspended in CM at a concentration of $10^6$/ml and incubated with an equal number of irradiated (30Gy) tumor cells for 20 hours at 37° C./5% $CO_2$. Stimulator tumor cells are restricted to the well characterised myeloid leukemia cell lines, U937, HL-60 and CTV-1 which are obtained from the DTMZ repository. Target cells in cytotoxicity assays include the NK-resistant RAJI cell line (obtained from the DTMZ cell bank), the breast cancer cell line MCF-7 (obtained from ATCC) and primary leukaemia cells from patients attending the Royal Free Hospital. Each myeloid leukemia line and the target cells are subjected to HLA typing as described above.

Cytotoxicity Assay

Target cells are recovered from culture or cryopreservation and washed in HBSS before resuspension in 1.0 ml of PHK-26 labelling diluent at a concentration of $4\times10^6$/ml. A 4 µl aliquot of PKH-26 is added to 1.0 ml of labelling diluent and then added to the cell suspension for 2 min at room temperature. The labelling reaction is stopped by the addition of 1.0 ml neat fetal calf serum for 1 min. Finally the labelled cells are washed twice in CM and resuspended in CM at $10^6$/ml. 50 000 PKH-26 labelled target cells in 100 µL RPMI 1640 (10% FCS) are added to 400 µL of effector cells and pelleted at 200 g for 1 min.

Cytotoxicity is measured in triplicate samples using a 4-hr cytotoxicity assay at 37° C. After the incubation period the cells are resuspended in a solution of To-Pro-3 iodide (Molecular Probes, Oregon, USA) in PBS (1 µM) and analysed by flow cytometry. At least 10 000 target cells are acquired with 1024 channel resolution after electronic gating on red fluorescence and the mean proportion of To-Pro iodide positive cells from the triplicate samples determined. Background target cell death is determined from cells incubated in the absence of effector cells. Cell-mediated cytotoxicity is reported as percentage killing over background cell death averaged from the three samples:

Mean(% cell lysis in test−% spontaneous lysis)

Less than 5% spontaneous lysis of target cells is observed in these experiments. In some experiments the labelling strategy is reversed, with the effector cells being labelled with PKH-26 and analysis of cell lysis being restricted to the PKH-ve fraction. This reversal confirmed that our initial findings are not due to an artefact of cell labelling.

Blocking Assay

PKH-labelled RAJI and K562 target cells are pre-incubated with rCD69 or control reagent (6 µg per $10^5$ cells) at 4° C. for 30 minutes prior to set-up of the T-ANK cytotoxicity assay described above.

Production and Purification of Recombinant Dimeric Human CD69

The extracellular domain of CD69 (residues 65-199) is amplified from cDNA by polymerase chain reaction using primers introducing XhoI and HindIII restriction sites and a stop codon (CD69 For 5' GCG CCT CGA GCA ATA CAA TTG TCC AGG CCA AT 3'; CD69Rev 5' CGC GAA GCT TAT TAT TTG TAA GGT TTG TTA CA 3'). The PCR product is subcloned into XhoI-HindIII restriction sites of pET-19b plasmid (Novagen) using standard techniques, to construct pET-19b/69. The DNA sequence that encodes the amino acid acceptor sequence for the E. coli BirA biotin protein ligase is added between the NdeI and XhoI sites of pET-19b/69 with the following primers 5' CAT ATG CAT GCG GGC GGC CTG AAT GAA ATT CTG GAT GGC ATG AAA ATG CTG TAT CAT GAA CTC GAG 3' and 5' CTC GAG TTC ATG ATA CAG CAT TTT CAT GCC ATC CAG AAT TTC ATT CAG GCC GCC CGC ATG CAT ATG 3'. DNA sequence is confirmed by automated sequencing using an ABI Prism 377 DNA sequencer.

Recombinant His-tagged human CD69 is expressed in BL21(DE3)pLysS (Novagen) at 37° C. Cultures are grown in 1 liter batches in 2×TY medium containing 100 µg/ml ampicillin and 34 µgml chloramphenicol. CD69 expression is induced by addition of 1 mM isopropyl-D-thiogalactopyranoside (IPTG) after the culture had reached an $OD_{600}$~0.6. Cells are allowed to grow for a further 4-5 hours and then harvested by centrifugation at 5000 g for 20 minutes at 4° C. Cell pellets are stored at −80° C.

Cell pellets from 250 ml culture are resuspended in 15 ml ice cold Resuspension Buffer (20 mM Tris-HCl pH 8.0). Cells are disrupted by multiple passages through a 16 gauge needle before centrifugation at 12000 g for 15 minutes at 4° C. The pellet is washed in Isolation buffer (20 mM Tris-HCl pH8.0, 500 mM NaCl, 2% Trition-X100, 2 M Urea) before being centrifuged again. This process is repeated once more. Pellets are finally washed in Resuspension buffer before being stored at −80° C.

Prior to purification and refolding, pellets are resuspended in Solubilization buffer (6M guanidinium hydrochloride, 20 mM Tris-HCl pH8.0, 500 mM NaCl, 10 nM imidazole) and passed through a 0.45 μm filter and then loaded onto a 5 ml Nickel loaded HiTrap Chelating column (GE Life science, Amersham UK) pre-equilibrated with Refolding buffer (20 mM Tris-HCl pH8.0, 500 mM NaCl, 6 M Urea, 10 mM imidazole). The protein is refolded by gradual removal of the urea through a linear gradient expanding from 100% Refolding buffer to 100% Wash buffer (20 mM Tris-HCl pH8.0, 500 mM NaCl, 10 mM imidazole). This is achieved with 250 ml buffer at 5 ml/minute using a HPLC system (Varian Technologies). After refolding, the protein is eluted with Elution buffer (20 mM Tris-HCl pH8.0, 500 mM NaCl, 500 mM imidazole).

Fractions are buffer exchanged into 10 mM Tris-HCl pH 8.0 using PD10 columns (GE Life science, Amersham, UK) and incubated with 2.5 μg BirA enzyme (Avidity Denver, USA) per 10 nmol substrate at 30° C. overnight following the manufacturers instructions. Excess biotin is removed and protein concentrated by washing with 50 mls HBSS in 10000 dalton MW cut-off centrifuge tubes (Vivascience UK) and assessed for rCD69 content by ELISA.

In order to assay CD69L expression by flow cytometry, 5 μg biotinylated rCD69 is conjugated to avidin coated yellow fluorescent beads (Spherotech Inc.) by rotating incubation at 4° C. for 40 minutes as previously described (Brown et al (1988) J. Exp. Med. 188: 2083-2090). Protein bead conjugates are briefly sonicated to prevent aggregation and incubated with $10^5$ target cells on ice for 60 minutes. Bound cells are washed with HBSS. Flow cytometric acquisition is performed at a maximum of 40 events per second in order to prevent acquisition of coincident events. Binding of 5 μg heat denatured rCD69 is used as a negative control for each experiment.

Example 9

Use of Activated NK Cells to Treat Poor Prognosis AML Patients

Miller et al (2005) as above, recently described method for giving NK cells from HLA haploidentical healthy donors to patients with relapsed AML after cyclophosphamide and Fludarabine chemotherapy. These patients showed NK cell engraftment, expansion and persistence in vivo.

The method described by Miller is adapted for use with the present invention by making the following changes:
(i) the allogeneic NK cells are pre-activated prior to infusion in accordance with the invention and using a process described below; and
(ii) NK cells will be selected from haploidentical related normal donors by direct immunomagnetic separation (CliniMACS).

The NK products infused in the Miller study were not pure (approximately 40% NK) and were contaminated with T and B cells. In one case, a patient died from EBV lymphoma derived from a B cell clone within the donor product which transformed in vivo during the lymphopaenic period post infusion.

When NK cells are selected from haploidentical related normal donors by direct immunomagnetic separation (CliniMACS), greater than 95% pure CD56+ cells is achieved. The degree of contaminating NKT cells is donor-dependent but is unlikely to exceed the dose of T cells infused in the Miller study. In the eventuality of a high NKT contamination, the NK dose infused may be reduced to ensure the T cell dose does not exceed that given by Miller. Alloreactive NK cells can be identified by CD69 expression in a MLR and such cells are phenotyped for KIR expression pre- and post culture prior to infusion. The present inventors have also established a skin explant model for graft-versus-host disease prediction. This in vitro assay may be used for quality assurance of NK cell infusions.

Leukaemic blasts are cryopreserved as viable cells from AML patients. Thus, donor NK products are tested in vitro for lytic activity against patient AML blasts and the results correlated with clinical response to treatment.

Patients are selected on the following criteria:
Adult capable of giving informed consent and having an HLA haploidentical donor Acute myeloid leukaemia beyond CR1 Ineligible for allogeneic HSCT from HLA-matched sibling or non-related donor Suitable for high dose chemotherapy with cyclophosphamide and Fluarabine Patients receive 60 mg/m$^2$ Cyclophosphamide and 25 mg/m$^2$ Fludarabine by daily i.v infusion for 5 consecutive days. On day five, the consenting donor undergo a single apheresis to obtain $2-3 \times 10^{10}$ mononuclear cells. NK cells are isolated by immunomagnetic selection using anti-CD56 microbeads (Miltenyi Biotec) and the CliniMACS device and incubated overnight with equal numbers of irradiated CTV-1 myeloid leukaemia cells to provide a tumour-specific stimulus.

After overnight incubation the cells are washed by centrifugation and viable NK cells enumerated. Doses of $5 \times 10^6$ NK/kg are prepared for the first 5 patients, $1 \times 10^7$/kg for the next five patients and $2 \times 10^7$/kg are prepared for the final group of five patients. Aliquots of donor NK cells are retained for testing as described above. Patients receive their donor NK cells as a single i.v infusion on day 6. They are monitored for clinical GvHD and cell specific chimerism studies are performed daily for the first 7 days; weekly for the next three months and monthly thereafter until 12 months.

Example 10

Production Schedule for Clinical Tumour-Activated NK Cells (T-aNK)

(i) Protocol for the Ex-Vivo Generation of T-aNKs
Normal, healthy, related donors are selected according to the same criteria as haematopoietic stem cell donors. Subject to informed consent, donors are screened for infectious disease markers according to JACIE standards and medically assessed for suitability to undergo apheresis. Each donor is additionally independently assessed by the apheresis sister.

Consenting donors undergo a single two-hour apheresis to harvest $25 \times 10^9$ mononuclear cells into ACD anti-coagulant. The apheresis collection bag is labelled with the donor name, donor hospital number, donor date of birth, recipient name, recipient hospital number, date and time of apheresis and volume of product. The apheresate is collected from the unit by a member of the LCT staff and transported directly in an approved container to the LCT.

On acceptance by the LCT, the apheresate is booked-in to the LCT product database and assigned a unique product number. The database reproduces all of the details on the product bag and additionally records the recipient date of birth, recipient body mass and the unique trial number assigned to the patient upon trial entry and consent.

Using routine SOP the apheresate is reduced to a pure mononuclear cell fraction by density gradient separation. A 1 ml sample is removed to obtain a mononuclear cell count and a CD56+ cell enumeration by flow cytometry. The volume of mononuclear cell fraction required to provide $2 \times 10^7$ NK/kg patient body mass is recovered into a 250 ml sterile bag, washed by centrifugation and resuspended at $5 \times 10^6$/ml in RPMI 1640 media, supplemented with 10% foetal calf serum (batches approved for pharmaceutical use)—all media supplied by Gibco Ltd, Paisely).

ii) Preparation of Cell Membranes from CTV-1 Cell Line

CTV-1 cells (supplied direct from the DSMZ tissue bank, Braunschweig, Germany—master cell bank record attached) are maintained in continuous exponential growth at a conc. of $0.5-1\times10^6$/ml in RPMI 1640 medium/10% FCS, in a closed culture system (Lifecell bags, Baxter Healthcare) in the Paul O'Gorman Laboratory of Cellular Therapeutics, RFUCMS (MHRA Accredited Tissue Bank 0029/00/00/0-03). Production records are maintained for all batches which include the batch numbers of all reagents and disposables used and the initials of all staff who performed individual procedures and the dates of those procedures. The serial numbers of all equipment used in the production process are also recorded.

To prepare the cell membranes, 8 ml aliquots are transferred by closed procedure into sterile 10 ml Cryocyte bags (Baxter Healthcare) and placed in a −80 freezer for 15 mins. Cells are quickly thawed in a 37° C. waterbath and then returned to the −80 freezer for a further 15 mins. Cells are again quickly thawed in the waterbath. 40 μl Pulmozyme (1,000 U/ml stock) is added to each culture bag which are then incubated at 37° C. for 30 minutes.

After washing by centrifugation at 2,500×g for 10 minutes to remove DNAse, the membrane preparations are resuspended in 4 mls sterile saline (infusion grade) and autoclaved to 121° C. for 5 mins. After cooling to 21° C. the bags are placed in a sonication bath for 25 seconds to disrupt aggregates which can form during autoclaving.

Figure 10:
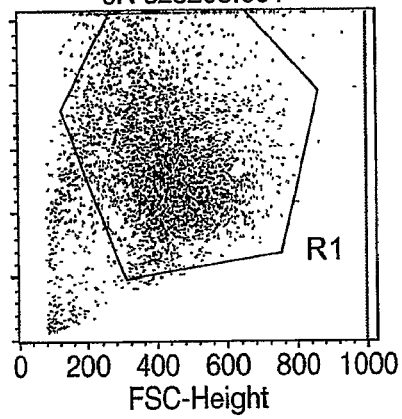
FIG. 10 is a scatter diagram showing an example of formation of cell membranes from CTV-1 cell line
Figure 10:
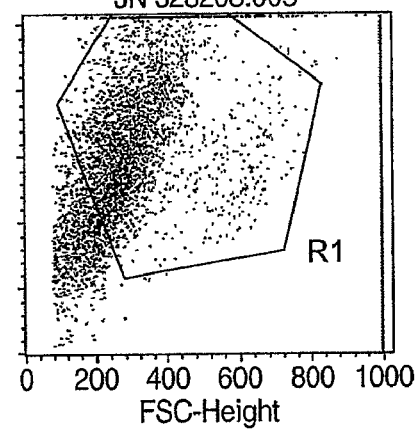
Figure 10:
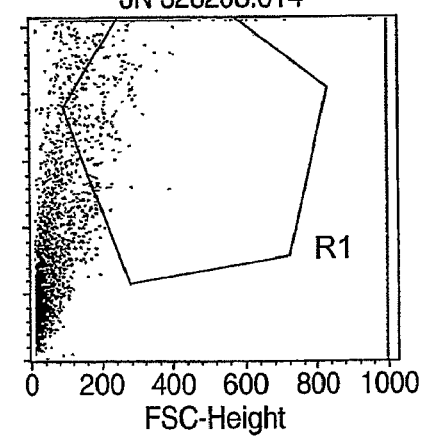

Formation of cell membranes is monitored by taking samples at various stages of the procedure and comparing them with forward angle light scatter (FSC) and 90° light scatter (SSC) of whole CTV-1 cells by flow cytometry. An example is shown in FIG. 10.

The membrane preps are batch-tested for sterility following routine SOP and stored at a total protein concentration of 5 mg/ml in sterile saline (for injection) at −80° C. in a controlled freezer labelled: "CTV-1 Membrane Preparation—Clinical Grade. Store below −40° C." together with the batch number, date of production and expiry date (6 months from date of manufacture).

(iii) Activation of Donor NK with CTV-1 Membrane Preparations

Lifecell culture bags containing selected donor mononuclear cells at $5\times10^6$/ml are supplemented with thawed CTV-1 membrane preparation to a final concentration of 5 mg per $10^7$ donor NK cells. Sufficient mononuclear cells are cultured to provide a maximum cell dose of $10^7$ NK/kg patient body mass. Cell cultures are maintained for a minimum of 16 hours and a maximum of 26 hours at 37° C./5% $CO_2$ in a Hepa filtered monitored incubator within the LCT.

After the overnight incubation, mononuclear cells are recovered by centrifugation, resuspended in labelling buffer (details) and incubated with clinical-grade anti-CD56 microbeads (Miltenyi Biotec GmbH) for 45 mins at 21° C. CD56+ NK cells are isolated by immunomagnetic selection by CliniMACS (Miltenyi Biotec GmbH). The NK+ fraction is recovered from the column after extensive washing (Cell Enrichment Procedure v3.02, Miltenyi Biotec, GmbH) to remove CD56-ve cells and residual CTVL membrane preparation. CD56+ cells are recovered and suspended in RPMI1640 at $10^8$/ml. Cells are cryopreserved following routine SOP in a single aliquot at the dose required. Aliquots are removed for quality assurance testing prior to cryopreservation:
Cell Number
CD56+ Cell Purity (Greater that 75%)
CD3+/CD56− T cell contamination (below $10^5$/kg patient body mass)

Anaerobic/aerobic bacterial culture ("negative" prior to release of product)
Detectable TaNK activity against NK-resistant cell line Raji in a four hour cytotoxicity assay (determined by >25% increase in Raji lysis compared to matched NK cells from same donor).

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

The invention is further described by the following numbered paragraphs:

1. A method for activating a Natural Killer (NK) cell, which comprises the step of contacting the NK cell in vitro with an activating tumour cell preparation (ATCP).

2. A method according to paragraph 1, wherein the ATCP comprises intact tumour cells.

3. A method according to paragraph 1, wherein the ATCP comprises a cell membrane preparation.

4. A method according to paragraph 1, wherein the ATCP comprises CTV-1 myeloid leukemia cells or a membrane preparation thereof.

5. A method according to any preceding paragraph, wherein, during activation, expression of CD69 is upregulated on the NK cell.

6. An activated NK cell produced by a method according to any preceding paragraph.

7. A composition comprising a plurality of activated NK cells according to paragraph 6 for treating a subject in need of same.

8. A composition according to paragraph 7, wherein some or all of the activated NK cells are autologous.

9. A composition according to paragraph 7, wherein some or all of the NK cells are allogeneic.

10. A composition according to paragraph 9, wherein the donor NK cells are HLA mismatched.

11. The use of a composition according to any of paragraphs 7 to 10 in the manufacture of a medicament for the treatment of cancer.

12. A method for treating cancer which comprises the step of administering a composition according to any of paragraphs 7 to 10 to a subject.

13. A method according to paragraph 12, wherein the subject is unsuited to invasive cancer treatment.

14. A use or method according to any of paragraphs 11 to 13, wherein the cancer is selected from the following group: Acute myeloid leukaemia (AML); Chronic lymphocytic leukemia (CLL); Lymphoma; or Breast cancer.

15. A method for determining whether a tumour cell preparation (TCP) is an activating tumour cell preparation (ATCP), the method comprising the following steps:
  (i) contacting the tumour cell preparation with a NK cell;
  (ii) contacting the NK cell from step (i) with a target cell resistant to lysis by non-activated NK cells;
  (iii) determining whether the target cell is lysed by the NK cell from step (i).

16. A method for determining whether a tumour cell preparation (TCP) is an activating tumour cell preparation (ATCP), the method having the following steps:

(i) contacting the tumour cell preparation with a NK cell;
(ii) determining whether the TCP causes upregulation of CD69 on the NK cell.

Having thus described in detail preferred embodiments of the present invention, it is to be understood that the invention defined by the appended claims is not to be limited to particular details set forth in the above description, as many apparent variations thereof are possible without departing from the spirit or scope of the present invention. Modifications and variations of the method and apparatuses described herein will be obvious to those skilled in the art, and are intended to be encompassed by the following claims.

The invention claimed is:

1. A method for activating a human Natural Killer (NK) cell, which comprises the step of contacting the human NK cell in vitro with an activating tumor cell preparation (ATCP) comprising intact tumor cells or a membrane preparation thereof; wherein said contact activates said human NK cell to lyse a target cell previously resistant to NK-cell lysis.

2. A method according to claim 1, wherein the ATCP comprises CTV-1 myeloid leukemia cells or a membrane preparation thereof.

3. A method according to claim 1, wherein, during activation, expression of CD69 is upregulated on the NK cell.

4. A method according to claim 1, wherein the NK cell is autologous.

5. A method according to claim 1, wherein the NK cell is allogeneic.

* * * * *